US011298462B2

(12) United States Patent
Atterbury et al.

(10) Patent No.: US 11,298,462 B2
(45) Date of Patent: Apr. 12, 2022

(54) AUTOMATIC INJECTION SYSTEM

(71) Applicant: Eli Lilly and Company, Indianapolis, IN (US)

(72) Inventors: William Godwin Atterbury, Columbus, OH (US); Joseph Daniel Dennis, Jr., Sandy Springs, GA (US); Brian Charles Kelley, Pataskala, OH (US); Mark Lafever, Indianapolis, IN (US); Steven Michael Madland, Columbus, OH (US); Andrew Thomas Snow, Fishers, IN (US); Jessica Diane Young, Columbus, OH (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/962,739

(22) PCT Filed: Mar. 6, 2020

(86) PCT No.: PCT/US2020/021321
§ 371 (c)(1),
(2) Date: Jul. 16, 2020

(87) PCT Pub. No.: WO2020/190529
PCT Pub. Date: Sep. 24, 2020

(65) Prior Publication Data
US 2021/0275745 A1    Sep. 9, 2021

Related U.S. Application Data

(60) Provisional application No. 62/818,889, filed on Mar. 15, 2019.

(51) Int. Cl.
*A61M 5/20* (2006.01)
*A61M 5/31* (2006.01)
(Continued)

(52) U.S. Cl.
CPC ........ *A61M 5/2033* (2013.01); *A61M 5/3148* (2013.01); *A61M 5/31513* (2013.01); *A61M 5/31581* (2013.01); *A61M 5/32* (2013.01)

(58) Field of Classification Search
CPC .............. A61M 5/2033; A61M 5/3148; A61M 5/31513; A61M 5/31581; A61M 5/32
See application file for complete search history.

(56) References Cited

U.S. PATENT DOCUMENTS

| 6,746,429 B2 * | 6/2004 | Sadowski ............... A61M 5/20 604/198 |
| 7,270,667 B2 | 9/2007 | Faccioli et al. |

(Continued)

FOREIGN PATENT DOCUMENTS

| EP | 2130561 | 12/2009 |
| WO | 2009040602 | 4/2009 |
| WO | 2020058729 | 3/2020 |

OTHER PUBLICATIONS

Patent Cooperation Treaty Written Opinion of the International Searching Authority pertaining to International Application No. PCT/US2020/021321; International Filing Date: Mar. 6, 2020; dated May 11, 2020.

(Continued)

*Primary Examiner* — Rebecca E Eisenberg
*Assistant Examiner* — Mark A Igel
(74) *Attorney, Agent, or Firm* — M. Daniel Spillman

(57) ABSTRACT

An automatic injection device is provided, where the device includes a syringe carrier and a retraction assembly. The syringe carrier includes two identical parts that are discrete from one another and interlock with one another. The retraction assembly includes a shuttle and a follower, the follower having a moveable latch. The follower has a coupled configuration in which the latch is biasedly coupled (Continued)

to the shuttle, and a decoupled configuration in which the latch is in sliding engagement with a curvilinear surface of the shuttle.

19 Claims, 27 Drawing Sheets

(51) Int. Cl.
*A61M 5/315* (2006.01)
*A61M 5/32* (2006.01)

(56) References Cited

U.S. PATENT DOCUMENTS

| | | | |
|---|---|---|---|
| 7,392,735 | B2 | 7/2008 | Brass et al. |
| 7,918,824 | B2* | 4/2011 | Bishop .................. A61M 5/24 604/136 |
| 8,016,795 | B2 | 9/2011 | Barrelle et al. |
| 8,075,535 | B2 | 12/2011 | Carrel et al. |
| 8,409,138 | B2* | 4/2013 | James ................ A61M 5/2033 604/110 |
| 8,733,593 | B2 | 5/2014 | Brem et al. |
| 8,734,394 | B2 | 5/2014 | Adams et al. |
| 9,044,549 | B2 | 6/2015 | Niklasson |
| 9,044,553 | B2 | 6/2015 | James et al. |
| 9,095,657 | B2 | 8/2015 | Holmqvist |
| 9,192,724 | B2 | 11/2015 | Fourt et al. |
| 9,402,957 | B2 | 8/2016 | Adams et al. |
| 9,872,961 | B2 | 1/2018 | Fourt et al. |
| 9,913,943 | B2 | 3/2018 | Fourt et al. |
| 9,962,493 | B2 | 5/2018 | Guthart |
| 10,052,437 | B2 | 8/2018 | Duinat et al. |
| 10,118,001 | B2* | 11/2018 | Fourt .................. A61M 5/3204 |
| 10,195,348 | B2 | 2/2019 | Komann |
| 10,265,476 | B2 | 4/2019 | Laiosa et al. |
| 10,363,377 | B2 | 7/2019 | Atterbury et al. |
| 10,434,258 | B2 | 10/2019 | Hourmand et al. |
| 10,639,425 | B2 | 5/2020 | Wang et al. |
| 10,702,661 | B2 | 7/2020 | Perthu |
| 10,835,668 | B2 | 11/2020 | Novickoff et al. |
| 2005/0203464 | A1 | 9/2005 | Haider et al. |
| 2007/0049872 | A1 | 3/2007 | Watts et al. |
| 2008/0108952 | A1 | 5/2008 | Horvath et al. |
| 2012/0004608 | A1* | 1/2012 | Lesch, Jr. ............. A61M 5/484 604/135 |
| 2012/0022466 | A1* | 1/2012 | James ................ A61M 5/3158 604/198 |
| 2012/0107783 | A1* | 5/2012 | Julian ................ A61M 5/3204 434/262 |
| 2012/0123350 | A1* | 5/2012 | Giambattista ....... A61M 5/2033 604/198 |
| 2012/0209192 | A1* | 8/2012 | Alexandersson ..... A61M 5/326 604/135 |
| 2013/0018325 | A1* | 1/2013 | Schiller ............... A61M 5/3137 604/198 |
| 2013/0046246 | A1* | 2/2013 | Cross .................. A61M 5/3272 604/189 |
| 2013/0138048 | A1* | 5/2013 | Kemp .................... A61M 5/24 604/196 |
| 2013/0138049 | A1* | 5/2013 | Kemp ................ A61M 5/2033 604/197 |
| 2013/0150800 | A1* | 6/2013 | Kemp ................ A61M 5/2033 604/192 |
| 2013/0204195 | A1* | 8/2013 | Ekman ................ A61M 5/326 604/197 |
| 2013/0204229 | A1* | 8/2013 | Olson .................. A61M 5/315 604/506 |
| 2013/0237921 | A1* | 9/2013 | Lannan ............... A61M 5/2033 604/198 |
| 2013/0281935 | A1* | 10/2013 | Kemp ................ A61M 5/3202 604/197 |
| 2013/0303985 | A1* | 11/2013 | Wotton .............. A61M 5/2033 604/115 |
| 2013/0310759 | A1* | 11/2013 | Hourmand ........ A61M 5/31511 604/198 |
| 2013/0317448 | A1* | 11/2013 | Hourmand .......... A61M 5/2033 604/197 |
| 2013/0345643 | A1* | 12/2013 | Hourmand ......... A61M 5/3232 604/198 |
| 2014/0236084 | A1* | 8/2014 | Adams ................ A61M 5/326 604/135 |
| 2016/0001004 | A1 | 1/2016 | Fourt et al. |
| 2016/0008542 | A1* | 1/2016 | Hirschel ................ A61M 5/24 604/137 |
| 2016/0151583 | A1 | 6/2016 | Liscio et al. |
| 2016/0346483 | A1 | 12/2016 | Fourt et al. |
| 2017/0072142 | A1* | 3/2017 | Perthu .................. A61M 5/002 |
| 2017/0224926 | A1* | 8/2017 | Dennis, Jr. .......... A61M 5/3202 |
| 2017/0224929 | A1 | 8/2017 | Sampson et al. |
| 2017/0239419 | A1* | 8/2017 | McLoughlin ....... A61M 5/3137 |
| 2017/0354779 | A1* | 12/2017 | Atterbury ........... A61M 5/2455 |
| 2018/0318563 | A1 | 11/2018 | Brown et al. |
| 2019/0009026 | A1* | 1/2019 | Gonzalez ............ A61M 5/2033 |
| 2019/0015591 | A1 | 1/2019 | Morlok et al. |
| 2019/0030249 | A1* | 1/2019 | Gonzalez ............ A61M 5/3271 |
| 2020/0188589 | A1 | 6/2020 | Hawson et al. |
| 2021/0093787 | A1 | 4/2021 | Perot et al. |

OTHER PUBLICATIONS

Patent Cooperation Treaty International Search Report pertaining to International Application No. PCT/US2020/021321; International Filing Date: Mar. 6, 2020; dated May 11, 2020.

* cited by examiner

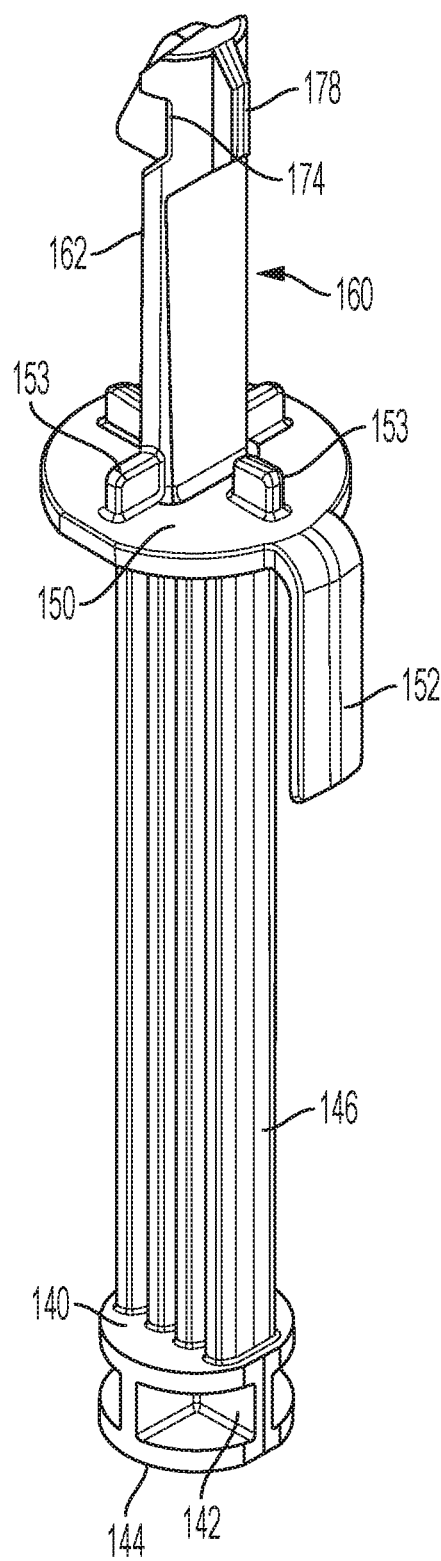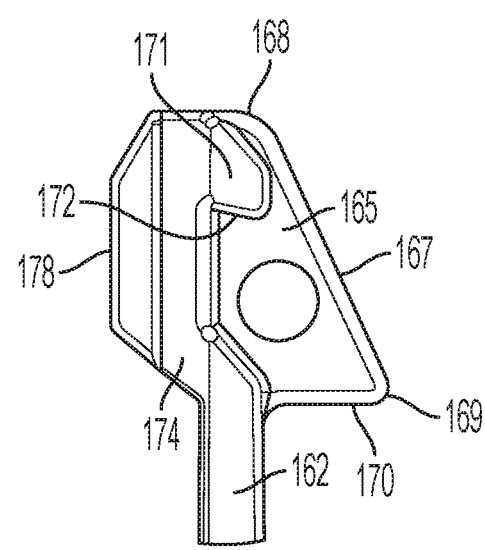
FIG. 4a
FIG. 4b

AUTOMATIC INJECTION SYSTEM

BACKGROUND

Aspects herein pertain to pharmaceutical injection devices, and, in particular, to automatic injection devices.

Patients suffering from a number of different diseases frequently must inject themselves with pharmaceuticals. A variety of devices have been proposed to facilitate these injections. One type of device is an automatic injection device. This type of device typically includes a trigger assembly that when operated by a user causes the device to automatically insert into the user a needle of a syringe that prior to triggering was disposed within the device housing, and then the device automatically injects a dose of medication through that inserted needle. The device may then automatically retract the syringe back into the device housing.

Some automatic injection devices include a syringe carrier that engages with a flange of a syringe. The syringe carrier may only support the flange or, in some cases, move the syringe between retracted and deployed positions. Some syringe carriers are of a single-piece construction. Some syringe carriers only partially surround the syringe, e.g. 270 degrees around the syringe, to leave an opening through which the syringe can be inserted radially.

Some automatic injection devices include retraction assemblies for auto-retraction of the syringe/needle combination. Retraction assemblies may include two components that slidably engage with one another. For example, to retract the syringe, one component rotatably slides against the other component. The inventors have recognized that such sliding contact can generate friction and/or friction variation along the sliding contact surfaces that may serve to impede retraction. Improvements to the syringe carrier and the retraction assemblies are described herein.

SUMMARY

In some embodiments, an automatic injection device includes a housing having a proximal end and a distal end, and a syringe including a needle, a syringe body and a plunger. The syringe is moveable within the housing from a first position to a second position that is distal to the first position to move the needle toward distal proximal end of the housing. The plunger is moveable relative to the syringe body to expel medication from the syringe body through the needle. The automatic injection device also includes a syringe carrier including two parts that are identical to one another, are discrete from one another, and are interlocked together. Each of the two parts has a proximal flange surface, a distal flange surface, a circumferential rounded wall between the proximal flange surface and the distal flange surface. A gap is located between the proximal flange surface, the distal flange surface, and the circumferential wall. A portion of the syringe body is received within the gap.

In another embodiment, an automatic injection device includes a housing, a syringe, and a syringe carrier. The housing includes a proximal end and a distal end. The syringe includes a needle, a syringe body and a plunger. The syringe body includes a syringe flange extending radially from the syringe body, and the plunger is moveable relative to the syringe body to expel medication from the syringe body through the needle. The syringe carrier includes a first part and a second part that are discrete from one another, and are interlockable together. Each of the first and second parts includes a proximal flange surface, a distal flange surface, a circumferential rounded wall extending between the proximal flange surface and the distal flange surface, a cushion disposed along a distal flange surface. The proximal flange surface and the distal flange surface having a greater material hardness than the cushion. A gap is defined by the proximal flange surface, the cushion, and the circumferential rounded wall, receiving a portion of the syringe flange. The cushions of each of the first and second parts together defining a ring shape to provide full circumferential support along the syringe flange.

In some embodiments, an automatic injection device includes a housing having a proximal end and a distal end, and a syringe including a needle, a syringe body and a plunger. The syringe is moveable within the housing from a first position to a second position that is distal to the first position to move the needle toward the distal end of the housing. The plunger is moveable relative to the syringe body to expel medication from the syringe body through the needle. The automatic injection device also includes a shuttle having a distal surface including a protrusion and a curvilinear surface. The curvilinear surface extends from the protrusion to define an undercut region. At least a portion of the distal surface is made of a lubricant-infused material. The automatic injection device also includes a follower having a follower body and a latch. The latch is moveable relative to the follower body and relative to the protrusion of the shuttle. The follower has a coupled configuration in which the latch is biasedly coupled over the protrusion. The follower also has a decoupled configuration in which the latch has cleared the protrusion and is in sliding engagement with the curvilinear surface, the follower is rotatable relative to the shuttle, and the shuttle is moveable toward the proximal end of the housing to retract the syringe.

These and other aspects will be apparent from the following description and claims.

BRIEF DESCRIPTION OF DRAWINGS

Aspects of the invention are described below with reference to the following drawings in which like numerals reference like elements, and wherein:

FIGS. 4a, 4b are respectively a perspective view and a partial side view of a plunger element shown separate from the other device components;

FIG. 6b is an exploded perspective view of the syringe carrier of FIG. 6a;

FIGS. 7a, 7b, 7c, 7d, 7e and 7f are respectively top right perspective, bottom right perspective, top, bottom, front, and rear views of one part of the syringe carrier of FIG. 6a;

FIG. 14 is an exploded view of the assembly of FIG. 13a;

FIG. 15b is another perspective view of the distal shuttle of FIG. 15a;

DETAILED DESCRIPTION

Figure 1:
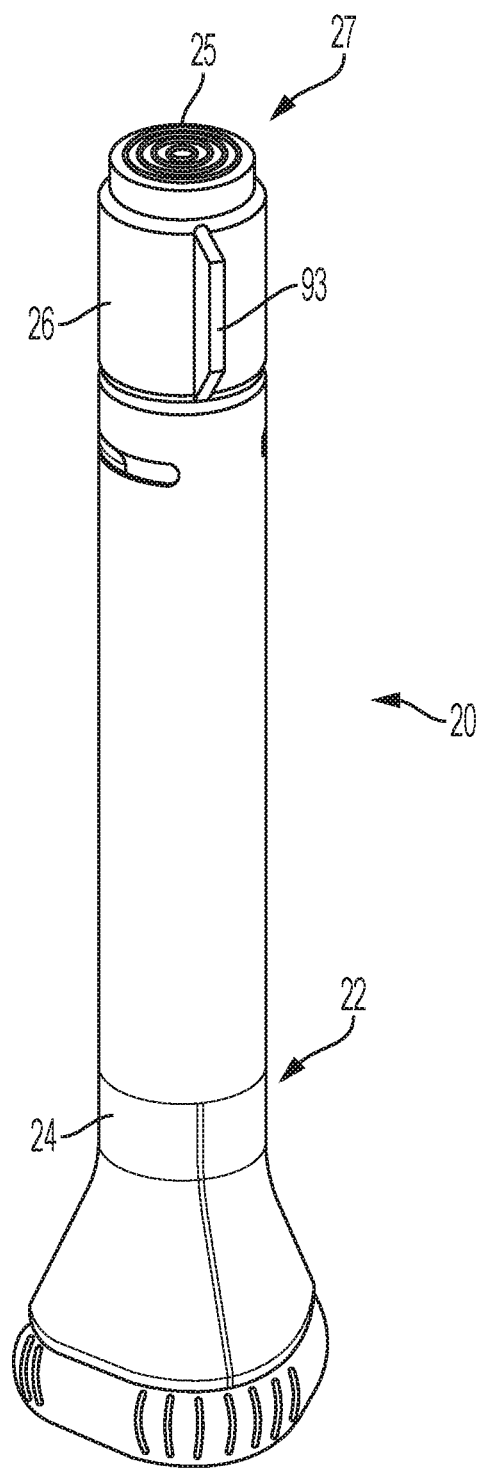
FIG. 1 is a side view of an automatic injection device with a trigger assembly of according to one embodiment, which device is shown in a locked arrangement prior to use.
Figure 2:
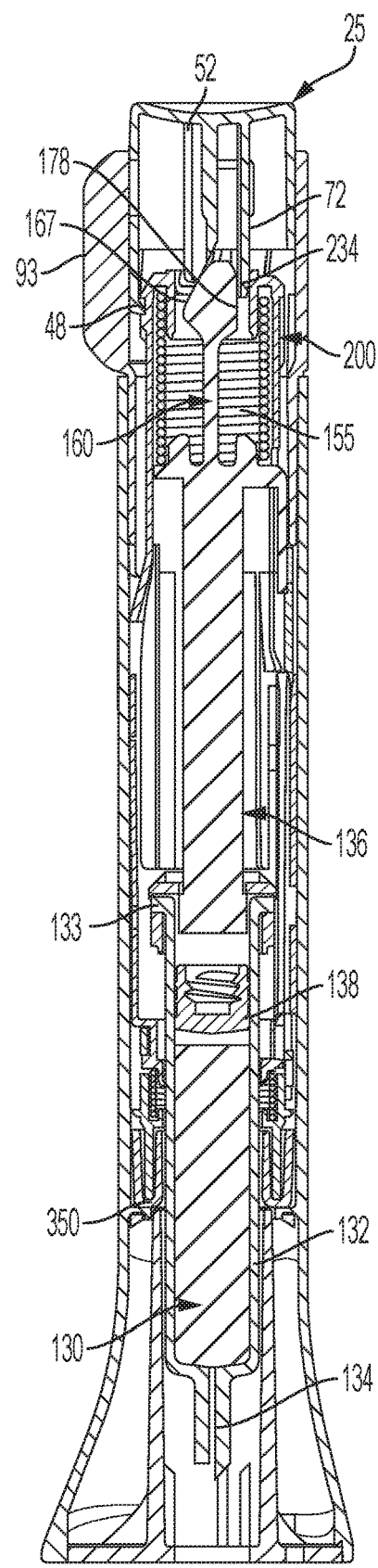
FIG. 2 is a longitudinal cross-sectional view of the automatic injection device of FIG. 1 with the overcap removed.

Referring now to FIGS. 1 and 2, there are shown different views of a first embodiment of an automatic injection device, generally designated 20, with a trigger assembly. When the trigger assembly is operated, the needled syringe of the device 20 is automatically driven downward such that the injection needle projects beyond the distal end of the device housing to penetrate the user. The device may then proceed to inject automatically, that is without further user action, the medication contents of the syringe through the needle, after which the syringe is retracted automatically such that the needle is returned to within the housing.

It will be appreciated from the following description that device 20 is conceptually similar in various aspects to the devices disclosed in U.S. Pat. No. 8,734,394, filed Feb. 24, 2011, and U.S. Pat. No. 9,872,961, filed Oct. 11, 2013, the disclosures of which are incorporated by reference herein in their entireties.

In the illustrative embodiment shown in FIG. 1, device 20 includes an outer housing 22 in which are operationally disposed working components of the device. The outer housing 22 may include a sleeve 26 and a main body 24 that may together form the axial height of the outer housing. Sleeve 26 may be rotatable relative to the main body 24 by the user. The sleeve may include a protruding fin 93 to facilitate rotation by a user. The device may include a button 25 that is part of the trigger assembly and that protrudes in the axial direction from the proximal end 27 of the housing. In some embodiments, when properly rotationally oriented by rotation of sleeve 26, the button 25 is unlocked such that the button can be depressed in the distal direction to start the automatic injection function of device 20. As used herein, distal and proximal refer to axial locations relative to an injection site when the device is oriented for use at such site, whereby, for example, distal end of the housing refers to the housing end that is closest to such injection site.

Figure 3:
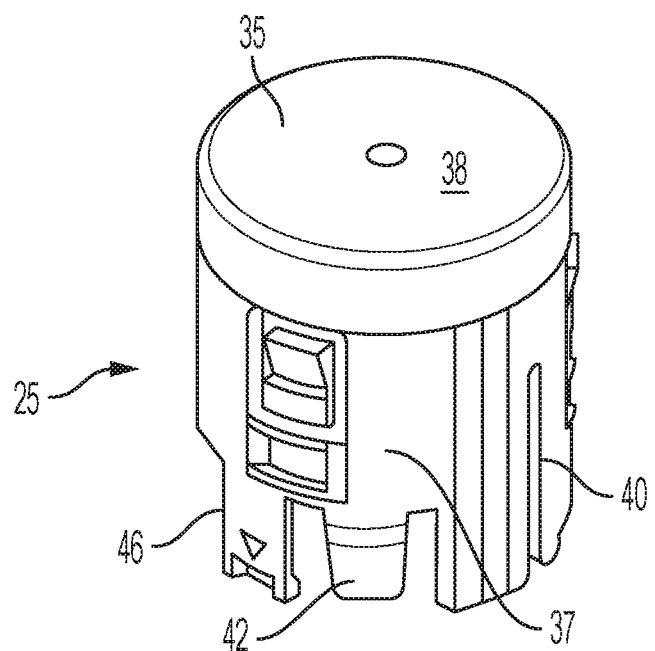
FIG. 3 is a perspective view of a button shown separate from the other components of the device of FIG. 1.

Button 25 may be molded as a single piece from a suitably durable material, such as Lustran ABS 348. As further shown in the illustrative embodiment of FIG. 3, button 25 may include a disc 35 with a skirt 37 extending distally from the outer periphery of disc 35. End disc 35 may have a flat proximal face 38 upon which a force can be directly applied by a user to selectively plunge the button to trigger the device. A notch 40 may be formed in skirt 37 at the distal end of the skirt 37, and may extend axially and form a slot which receives a rib of sleeve 26 so as to rotatably key together the button 25 and sleeve 26. A set of three equally angularly spaced resilient fingers 42 that may each be provided with a detent on its radially inward face may be provided at the base of skirt 37 for locating the button 25 on shuttle 200. Each finger 42 may be adjacent to one of three equally angularly spaced fingers 46 with inwardly angled stops 48 also provided in skirt 37 for attachment to shuttle 200.

Tapered flange portion 52 may have a sloped surface that serves as an actuating element of the trigger which cams a prong of the trigger to unlatch it for the trigger assembly. Differently designed actuating elements, including one that is not ramp shaped, can be used to cam and thereby unlatch the prong in alternate embodiments.

In some embodiments, device 20 includes a medication-filled syringe. As shown in FIG. 2, the syringe, generally designated 130, includes a barrel 132 with a flange 133, and an injection needle 134 mounted at the distal end of the barrel and in fluid communication with the medication contents of the barrel. Although needle 134 is shown as a single needle and is generally expected to be sized for subcutaneous delivery, with adaptions the device could be equipped with a needle of various sizes or types known in the art, including, but not limited to, a needle formed of one or more shortened injection needles, including microneedle arrays, and which needle allows for injection at different depths, such as intradermal.

Device 20 in general, and more particularly the technology claimed in this application, may be utilized in injecting a variety of medications or therapeutics into a person in need thereof. Syringes of the devices or claimed technology can be filled with any of a number of therapeutics. Device 20 may further comprise a medication, such as for example, within a reservoir within barrel 132 of syringe body or cartridge. In another embodiment, a system may comprise one or more devices including device and a medication. The term "medication" refers to one or more therapeutic agents including but not limited to insulins, insulin analogs such as insulin lispro or insulin glargine, insulin derivatives, GLP-1 receptor agonists such as dulaglutide or liraglutide , glucagon, glucagon analogs, glucagon derivatives, gastric inhibitory polypeptide (GIP), GIP analogs, GIP derivatives, oxyntomodulin analogs, oxyntomodulin derivatives, therapeutic antibodies, such as, for example, but not limited to treatment of psoriasis, ulcerative colitis, Chrohn's disease, pain, migraine, and any therapeutic agent that is capable of delivery by the above device. The medication as used in the device may be formulated with one or more excipients. The device is operated in a manner generally as described above by a patient, caregiver or healthcare professional to deliver medication to a person. The device, or claimed technology of this application, may then be operated in a manner generally as described above with respect to device 20 to inject a person with such therapeutic in the syringe.

The plunger mechanism may include a plunger element, generally designated 136, and an elastomeric sealing member or piston 138 that seals the medication within barrel 132.

Plunger element 136 may be molded as a single piece of a lightweight but sturdy and sufficiently resilient material, such as DELRIN 311DP from Dupont Engineering Polymers. As further shown in FIG. 4*a*, plunger element 136 includes a cylindrical foot 140 which may be hollowed so as to have a cruciform center 142. The distal face 144 of foot 140 operationally abuts piston 138 during plunger advancement. A ribbed bar 146 may rigidly or inflexibly extend axially upward from the top of foot 140 to a disc-shaped flange 150 that has a larger diameter than foot 140. A plunger arm 152 may be formed on the outer radial periphery of flange 150 and may extend axially and distally from flange 150 in spaced relationship with plunger bar 146.

Four equally angularly spaced bosses 153 may upwardly project from the flange 150. Bosses 153 may aid in centering the drive coil spring 155 shown in FIG. 2 that acts on flange 150 to bias plunger element 136 distally within device 20.

Plunger element 136 may include a resilient prong, generally designated 160, that serves as part of the trigger assembly. The single prong 160 may latchably engage a shuttle in the shown embodiment until released by the plunging of button 25, which release allows the spring 155 to bias the plunger element 136 distally to result in needle insertion and injection. In some embodiments, the plunger includes one and only one resilient prong. In other embodiments, however, the plunger may include more than one resilient prong.

Prong 160 may include an upstanding, tapering finger 162 that projects axially from the center of flange 150 so as to be centered on the axis of the housing 22. Finger 162 may be flexible due to its construction to allow its bending movement when the prong is acted on for its release. As shown in FIG. 4*b*, prong 160 may include a triangular projection 165 centered on the side to side width of finger 162. Projection 165 may include a ramp surface 167 extending proximally and at an angle inward from the tip 169 of the projection 165 to form an outward facing ramp used in camming of the prong for release. Ramp surface 167 extends from tip 169 to a proximal end 168. The distal face 170 of projection 165, which face does not serve a latching function, is transverse to the axial direction.

A pair of latching surfaces 172 may be provided on the proximal-most portions 171 of extensions 174 of finger 162. Latching surfaces 172 and extensions 174 flank either side of projection 165 and are spaced radially inward from the ramp surface 167 at the height of the latching surfaces along prong 160. Latching surfaces 172 are provided generally in axial alignment with finger 162 and each may be formed with a slight undercut so as to slope slightly distally as it extends in the radial direction toward ramp surface 167. Latching surfaces 172 are disposed at a height between the axial extent of ramp surface 167, such as near the proximal end 168. In this location, the contacting forces on the ramp surface may tend to produce a translational deflection of the latching element which may have a lower and more consistent unlatching force than would a rocking or pivoting motion, caused by the latching surfaces being substantially above or below the ramp surface, that would introduce extra deformation of prong 160 and make the unlatching motion less smooth.

The back surface of projection 165 may jut rearward beyond extensions 174 to define a safety protuberance 178. Protuberance may be backed up by safety arm 72 when button 25 is in its locked orientation.

Figure 5A:
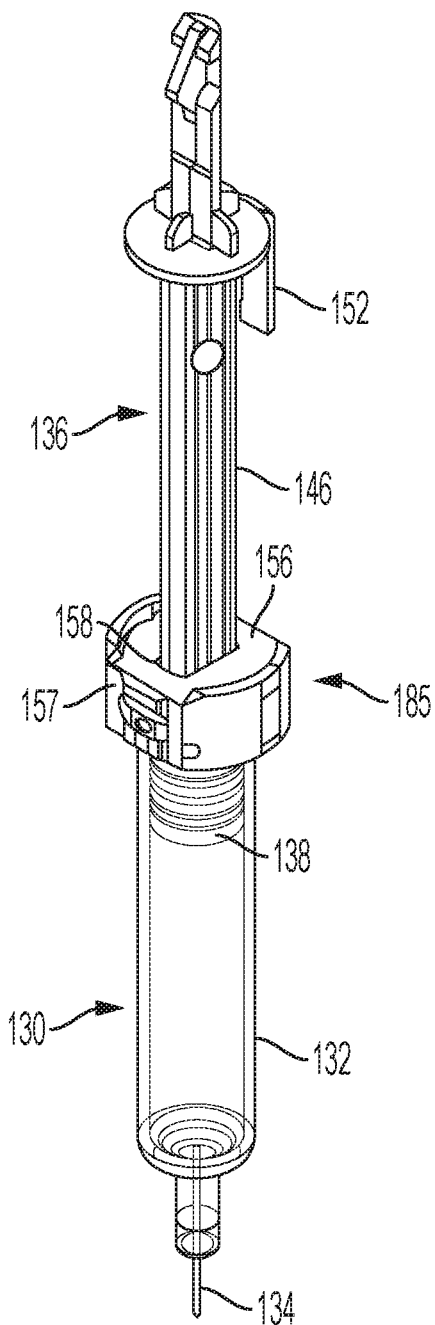
FIG. 5a is an assembly including a syringe, syringe carrier, and plunger element, with the syringe shown in phantom.
Figure 5B:
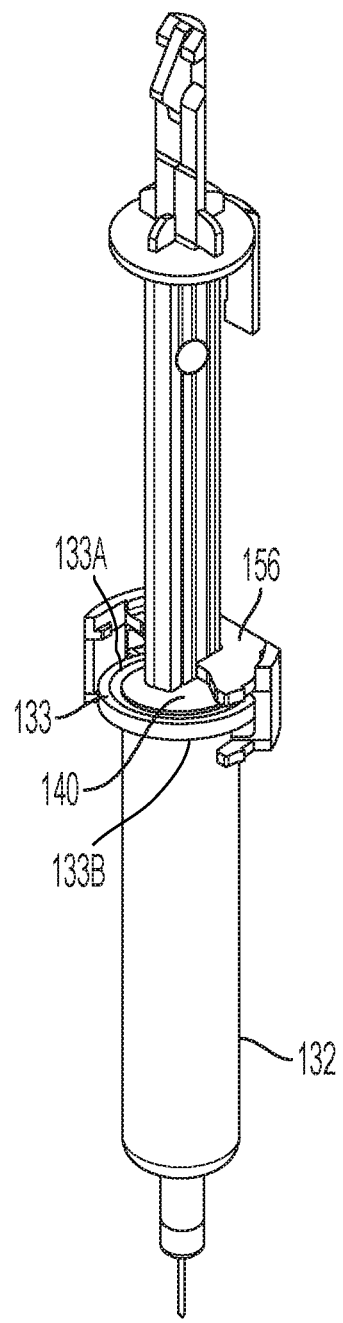
FIG. 5b is the assembly of FIG. 5a with one part of the syringe carrier hidden from view and the syringe shown in solid.
Figure 5C:
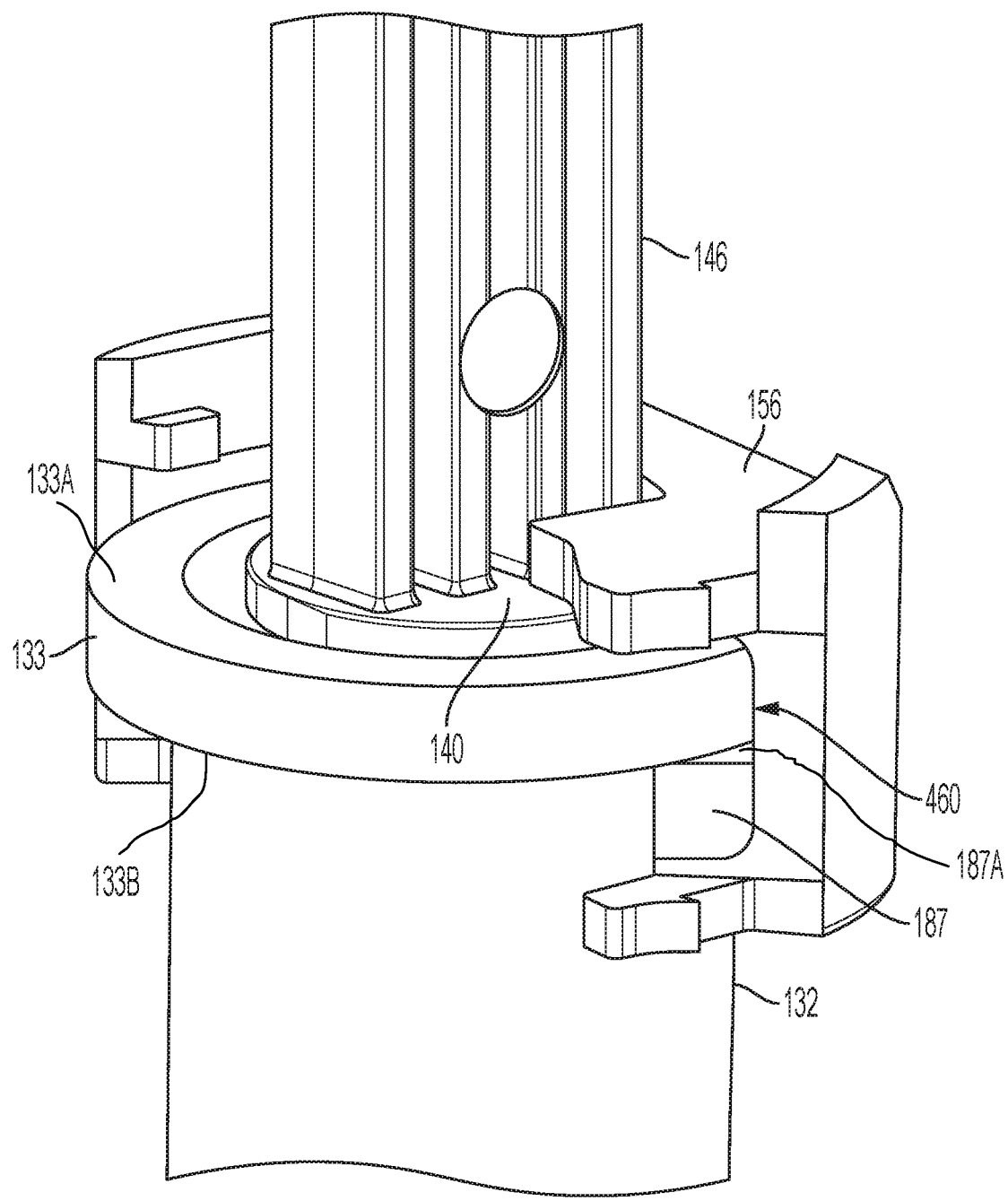
FIG. 5c is an enlarged view of a portion of FIG. 5b.

An assembly including the plunger element 136, syringe carrier 185, and syringe 130 is shown in FIG. 5*a*. The plunger bar 146 of the plunger element 136 extends through an opening 158 in the syringe carrier 185 and into the syringe carrier. As shown in FIGS. 5*b* and 5*c*, in which one part of the syringe carrier is hidden from view, the syringe carrier encloses a radial flange 133 of the syringe 130. As also seen in FIGS. 5*b* and 5*c*, the syringe carrier also encloses the foot 140 of the plunger element. The syringe carrier 185 may be configured to provide full, surrounding support of the syringe flange 133 of syringe 130. While such syringe carrier may be desired, designs of the syringe carrier which allow for manufacturing and assembly is also desirable in high-volume manufacturing settings.

Figure 6A:
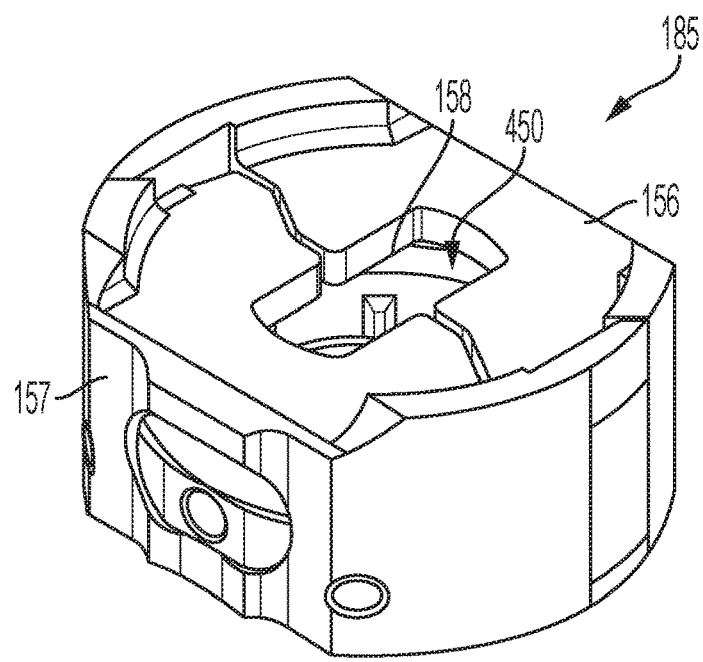
FIG. 6a is a perspective view of a syringe carrier separate from the other device components.
Figure 6B:
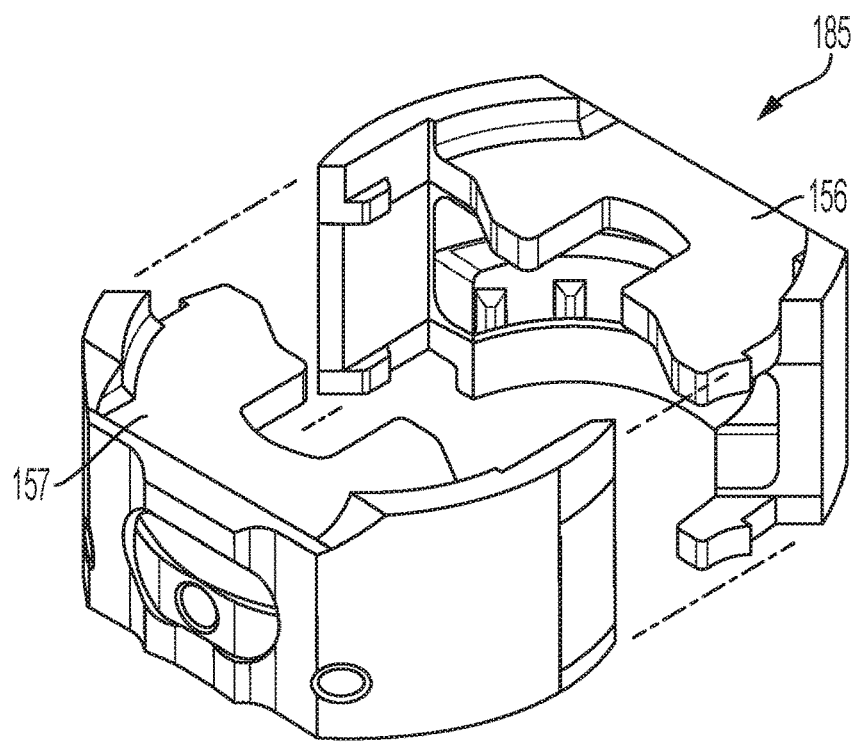

An illustrative embodiment of a fully assembled syringe carrier is shown in FIG. 6*a*. The syringe carrier may be made up of a first part 156 that couples with a second part 157. The parts 156, 157 may be coupled to one another by various attachment mechanisms, such as, for example, adhesives, such as bonding glue, ultrasonic welding, mechanical interlocking, and the like. An exploded view of the syringe carrier is shown in FIG. 6*b*. The two halves of the syringe carrier combine to define a cavity 450 that receives syringe flange 133 during device assembly such that the syringe carrier 185 surrounds the flange 133.

Figure 7A:
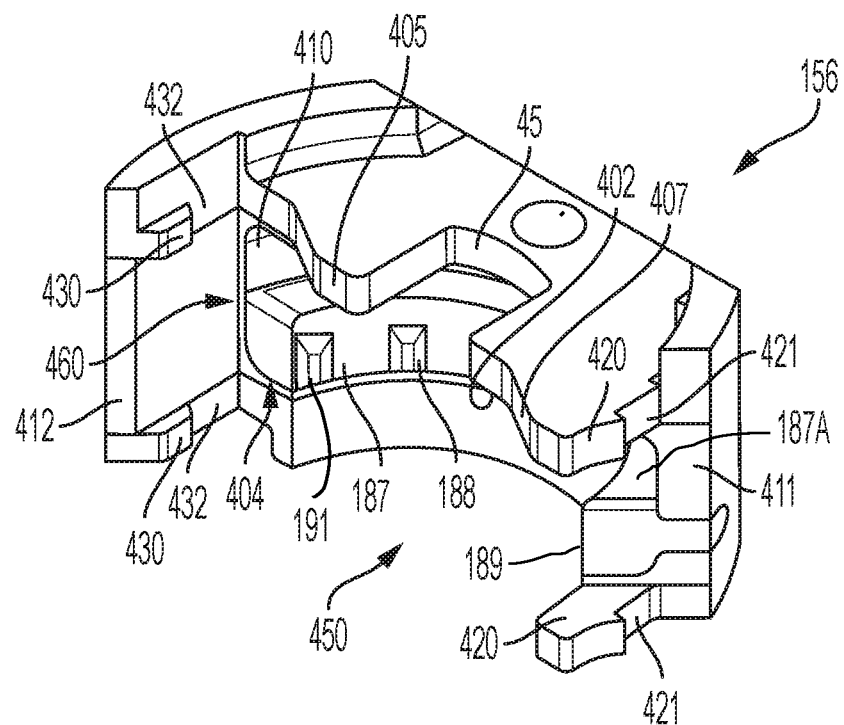
Figure 7B:
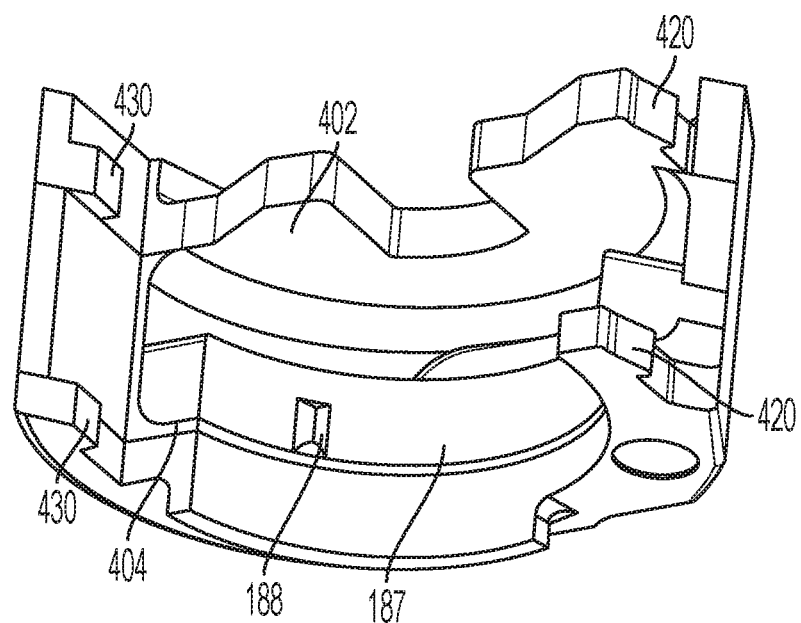

In some embodiments, the syringe carrier 185 is made up of two identical, interlocking parts. One embodiment of one of the parts is shown in FIG. 7*a*. The part shown in FIG. 7*a* is the first part 156 of the syringe carrier, but the second part 157 may also be identical to what is shown in FIGS. 7*a*-7*f*. Having the first and second parts be identical may have the benefit of requiring manufacture of only one shape, and may facilitate assembly of the syringe carrier by avoiding the need for a particular part being oriented at a specific side of the syringe carrier. Other embodiments of the parts having at least some of the features described herein may include parts that are not identical and still provide interlocking and support to the flange.

The first part 156 may include a proximal flange surface 402, a distal flange surface 404, and a circumferential rounded wall 410 disposed between the proximal flange surface 402 and the distal flange surface 404. An axial gap 460 is defined between the proximal flange surface 402 and the distal flange surface 404. The gap 460 is sized to receive the axial thickness of flange 133 (see FIG. 5*c*) of the syringe. The proximal flange surface 402 may include a proximal flange extending from the wall, and the distal flange surface 404 may include a distal flange extending from the wall in parallel with the proximal flange.

In some embodiments, the syringe carrier 185 may include a cushion 187 that defines a distal boundary for the gap 460. With reference to FIG. 5*c*, the distal surface of flange 133 of the syringe may rest against and be supported by the proximal surface 187A of cushion 187 when the flange is held by the syringe carrier. In some embodiments, the rest of the syringe carrier is made of a material having a greater hardness than that of cushion 187. The cushion 187 may provide shock absorbance or other impact attenuation to, e.g., reduce the likelihood of breakage of the syringe during actuation of the automatic injection device, and/or to soften the impact sound of the syringe against the syringe carrier during movement of the syringe. The cushion may be made by overmolding a material onto the syringe carrier.

The cushion may be formed of a compressible material, such as an elastomer or a closed cell foam.

In some embodiments, the cushion may be arc-shaped to fit with the shape of the circumferential rounded wall 410 and/or the shape of the distal flange surface 404. In some embodiments, the cushion 187 segments are configured and shaped, such as in a ring shape, to provide full circumferential, that is 360 degrees, support to the entire flange 133 when the parts 156, 157 are coupled. To this end, in some embodiments, the parts are shaped around the flange so that the cushion 187 can provide this full support to the flange 133, such as, for example, to withstand spring insertion drive forces.

In some embodiments, the syringe carrier 185 may include one or more protrusions extending radially inward, where the protrusions may facilitate centering of the syringe within the syringe carrier by contacting the syringe body underneath the syringe flange. In the embodiment shown in FIG. 7a, the syringe carrier includes a protrusion 188 that extends from an inner radial surface 189 of the cushion 187. The protrusion may be made from the same cushioning material as the cushion 187 and may be integrally formed with the cushion 187 as a single component. The protrusions may be radially compressed to a greater degree relative to any radial compression of the surface 189 by the syringe body. In the embodiment shown, the cushion 187 of each of the parts includes a pair of protrusions 188a and 188b (as shown in FIG. 7d) so that when the parts are coupled to one another the protrusions together help centering of the syringe at four points. In one example, the coupled parts define the four protrusions that are arranged spaced equally apart from one another. When parts are coupled, the number of protrusions provided can vary between two or more. In another embodiment, the one or more protrusions may optionally include the protrusion 191 that can be located along the inner radial surface 189 in closer proximity to a latch protrusion 430 than a prong 420, and in some embodiments, adjacent to the end of the inner radial surface 189 next to the latch protrusion as shown in FIG. 7a. In other embodiments, there may be a protrusion adjacent the end of the inner radial surface 189 next to the prong 420 in addition to, or instead of, the protrusion 191. Protrusion 191 may be included to support the syringe during the snap engagement of the two parts of the syringe carrier together, when the portion of the part 156 or 157, which includes the latch protrusions 430, flexes radially outward when mating with the prongs 420 of the other part. After the snap engagement, the protrusion 191 may also provide additional support to the syringe at a location where when mated there may be a gap between the cushions.

The proximal flange surface 402 may provide supportive engagement for the proximal surface of foot 140 of the plunger element.

Each part of the syringe carrier may define an opening portion 45 defined by radial plunger facing walls that forms one part of the opening 158 of the fully assembled syringe carrier. Such opening portion 45 may be shaped and sized to receive the shape and size of the plunger element in a manner to provide sliding support to the plunger body. In the example shown, the opening portion 45 in each part has a U-shape with opposing parallel planar sides coupled to one another by a rounded side.

The edges 405, 407 of the proximal flange surface of one of the parts of the syringe carrier disposed lateral relative to the opening portion 45 may be complementarily shaped to mate with the edges of the other of the parts, such as shown in FIG. 6a. The edges may have a planar shape. In the embodiment shown, each of the edges is non-linearly shaped including a protrusion and recess.

In some embodiments, each part of the syringe carrier 185 may include a first lateral wall end 411 and a second lateral wall end 412, where the circumferential rounded wall 410 extends from the first lateral wall end 411 to the second lateral wall end. In the embodiment shown, the first lateral wall 411 is disposed recessed relative to the edge 407, while the second lateral wall 412 is disposed protruding relative to the edge 405.

The syringe carrier 185 may include interlocking components that interlock to form the fully assembled syringe carrier. In some embodiments, the interlocking components extend from the lateral wall ends of each part of the syringe carrier. In the embodiment shown in FIGS. 7a and 7b, the interlocking components comprise prongs 420, each having an indentation 421, and latch protrusions 430, each having an accompanying slot 432. The prongs 420 may extend from one of the lateral walls, shown as the first lateral wall end 411, and the protrusions 430 extend from the other of the lateral walls, shown as the second lateral wall end 412. Each of the prong 420 and indentation 421 of the first part 156 of the syringe carrier are complementarily shaped and sized to mate with a corresponding protrusion 430 and slot 432 of the second part 157 of the syringe carrier to interlock the two parts of the syringe carrier together.

Figure 7C:
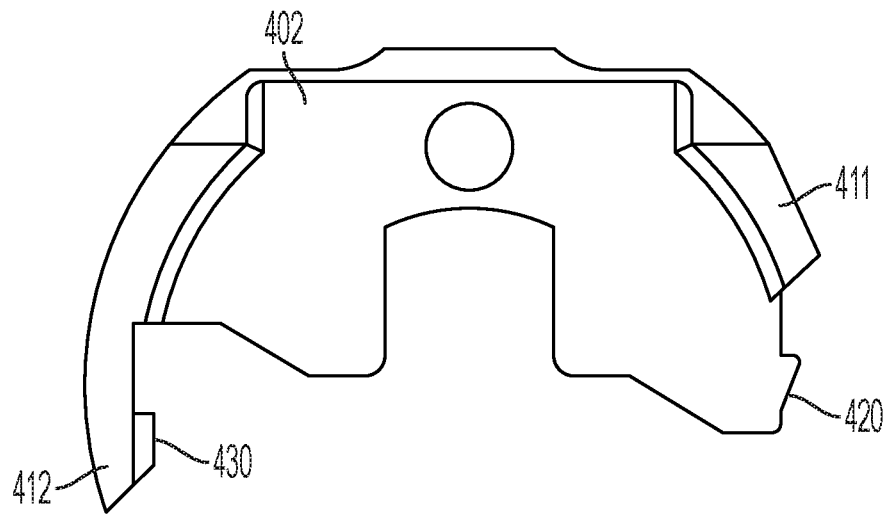
Figure 7D:
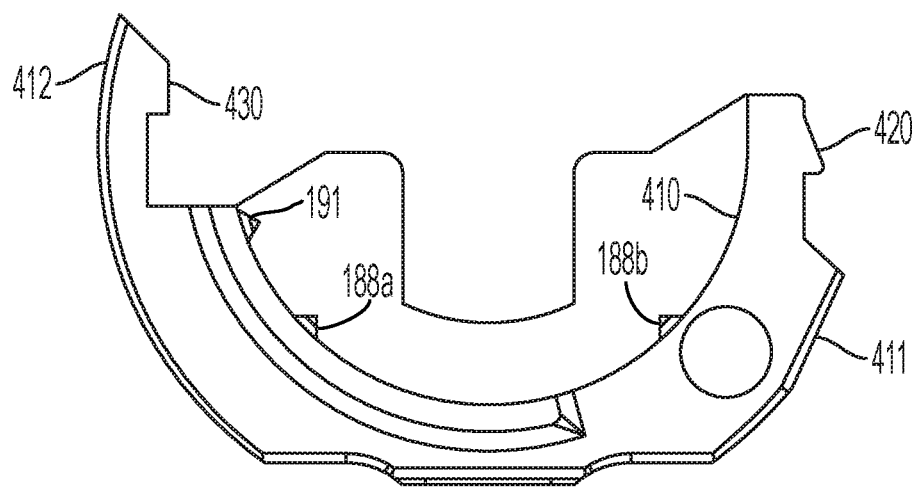
Figure 7E:
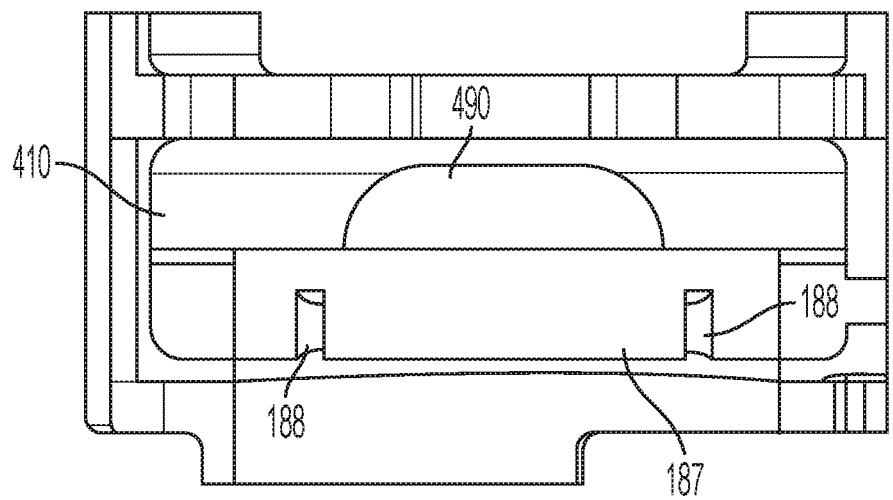
Figure 7F:
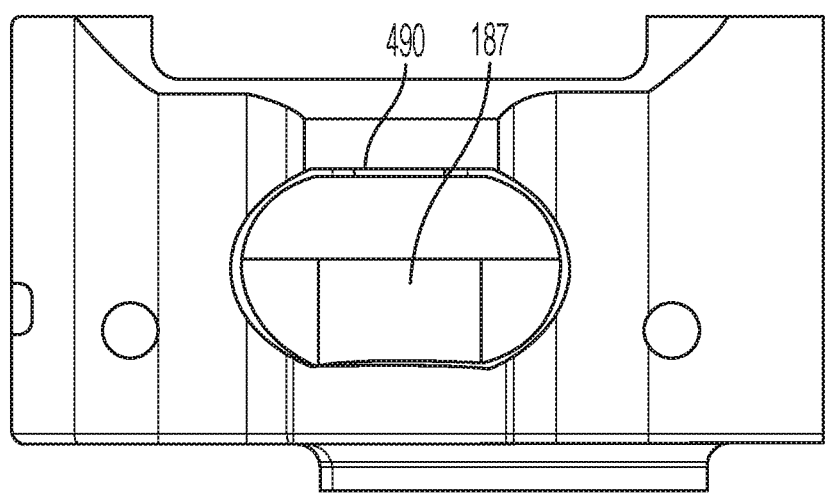

As seen from the top view in FIG. 7c and the bottom view in FIG. 7d, each part of the syringe carrier may be approximately C-shaped. As seen from the front view in FIG. 7e and the front view in FIG. 7f, the syringe carrier may include a window 490 that passes completely through the circumferential rounded wall 410 of the syringe carrier.

As best seen in FIG. 5a, the syringe carrier 185 may fully surround an outer perimeter of the syringe body, i.e. 360 degrees around the syringe body. The proximal and distal flange surfaces 402, 404 of each of the parts together fully overlap the proximal surface 133A and/or the distal surface 133B of the syringe flange 133, as shown in FIG. 5a. This configuration of a syringe carrier completely surrounding and/or overlapping the syringe flange may be advantageous when higher spring forces for driving the plunger are used by the delivery device, such as, for example, due to larger volume of medication, such as 2 to 3 mL, and/or higher viscous medications. Such configuration can allow for distribution of the drive force over a greater area of the syringe flange, which may help to reduce the likelihood of breakage of the syringe flange that are typically made of glass.

Figure 8:
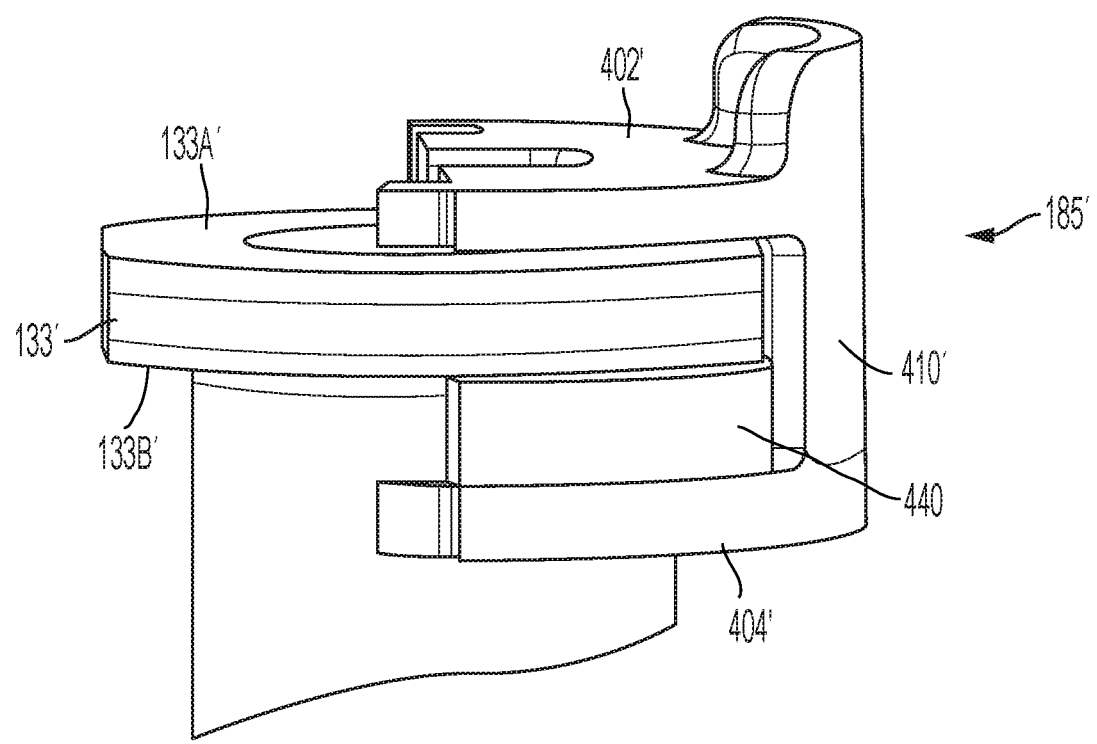
FIG. 8 is a perspective view of another embodiment of a syringe carrier mated with a syringe, with one part of the syringe carrier hidden from view.

It should be understood, however, that other configurations for the syringe carrier are possible. One alternative embodiment is shown in FIG. 8. In FIG. 8, one part of the syringe carrier 185' is removed to better see the flange 133' of the syringe interacting with the syringe carrier. The proximal flange surface 402' and the distal flange surface 404' of both parts of the syringe carrier 185' together may be configured to provide full 360 degree support to the syringe flange 133'. The syringe carrier may also include the cushion 440, shown disposed along the proximal surface of the distal flange surface 404'. When employed, the flange 133' would rest along the cushion in a position in between the cushion and the proximal flange surface 402'.

Figure 9A:
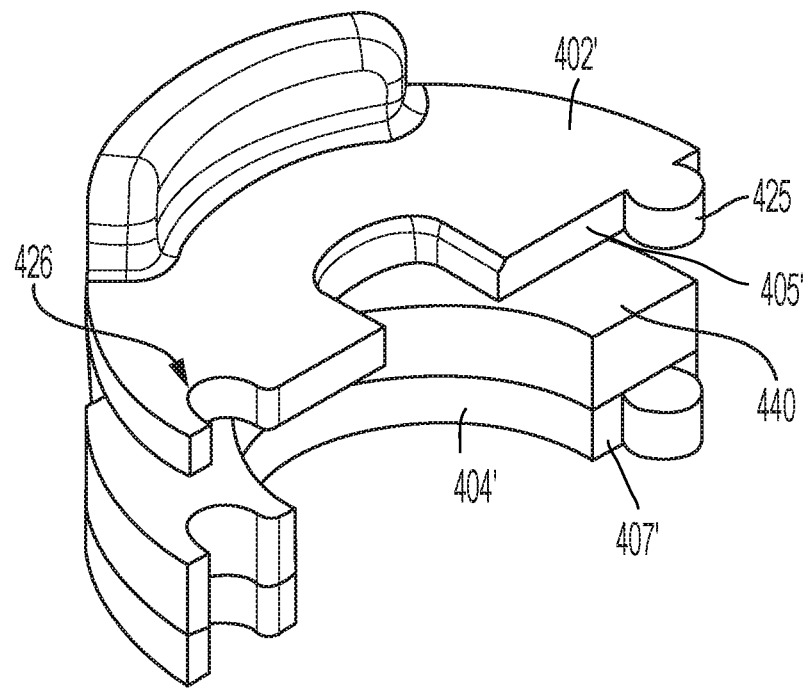
FIG. 9a is a perspective view of the part of the syringe carrier of FIG. 8.
Figure 9B:
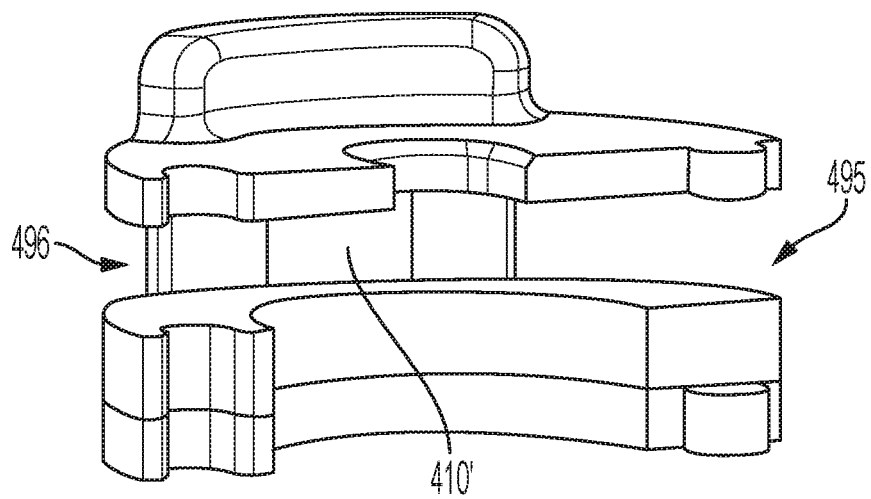
FIG. 9b is another perspective view of the part of the syringe carrier of FIG. 8.
Figure 10:
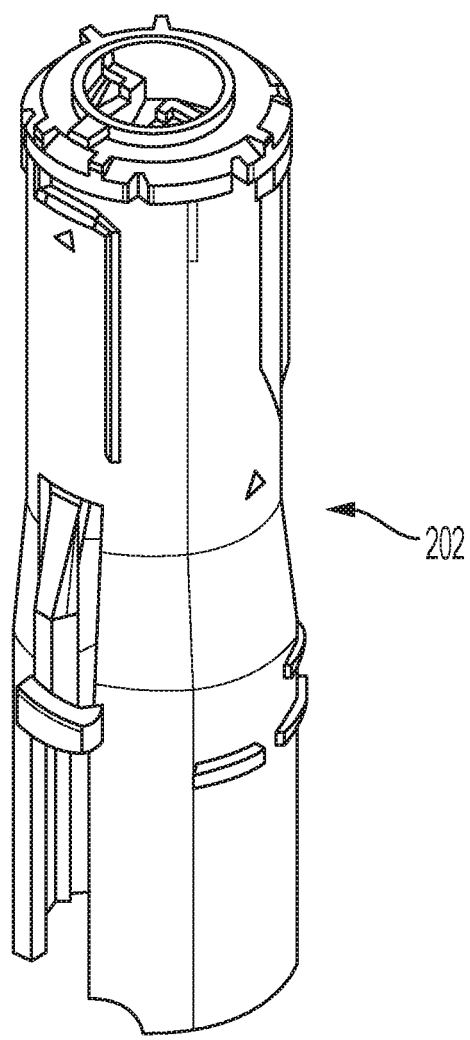
FIG. 10 is a perspective view of a proximal shuttle part shown separate from the other device components.
Figure 11A:
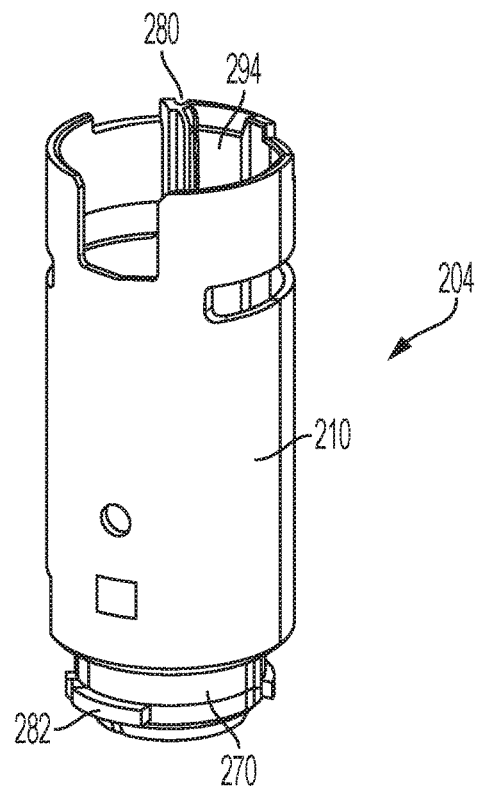
FIGS. 11a, 11b, 11c, 11d and 11e are respectively perspective, first side, longitudinal cross-sectional, top and bottom views of a distal shuttle part shown separate from the other device components.
Figure 11B:
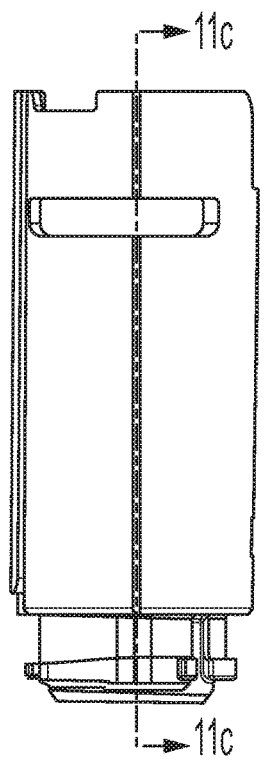
Figure 11C:
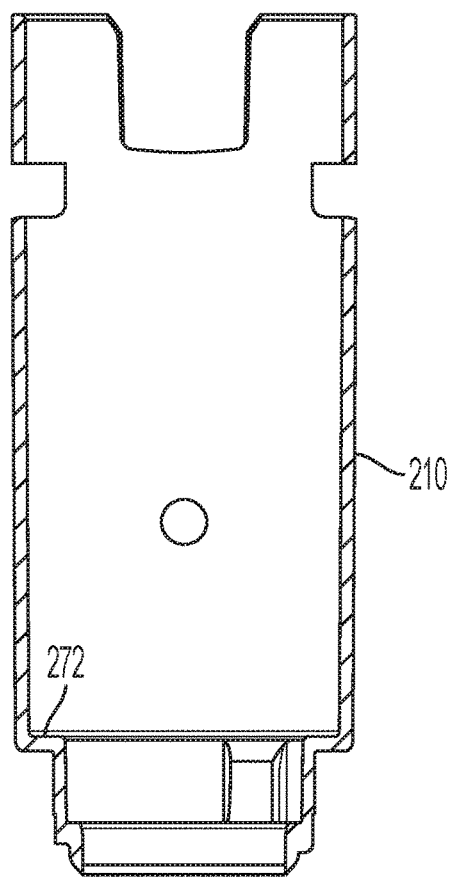
Figure 11D:
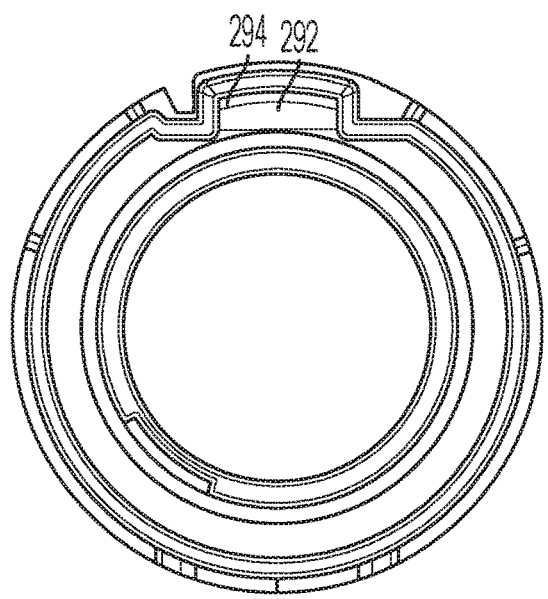
Figure 11E:
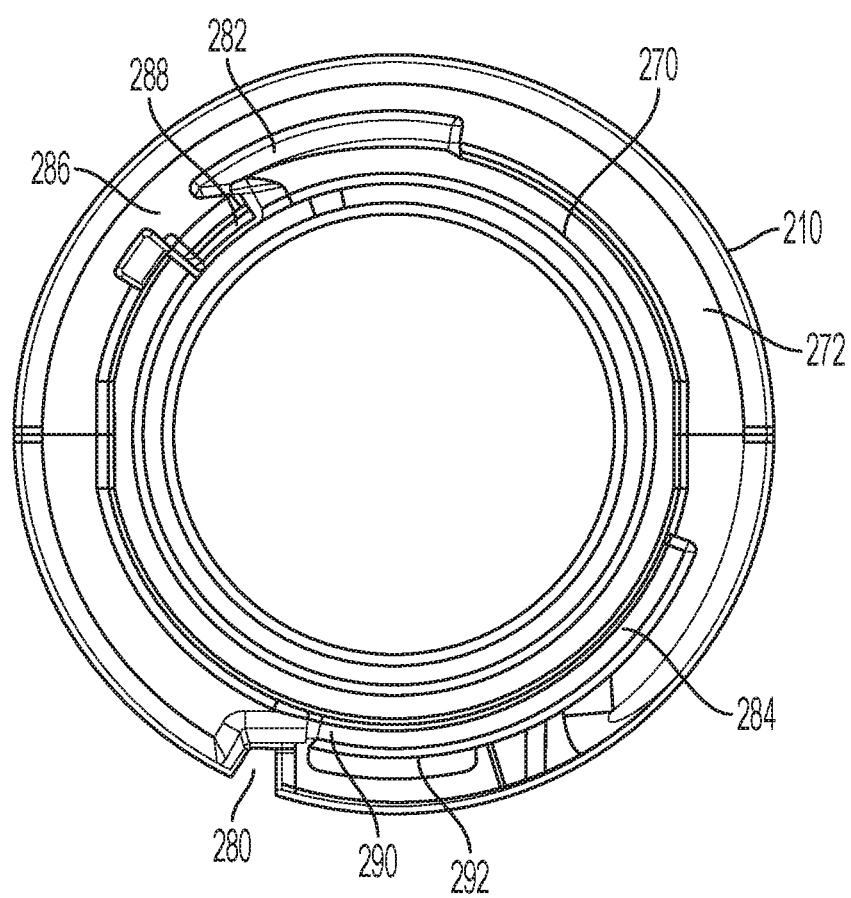

As seen in FIGS. 9a-9b, in this embodiment, the syringe carrier 185' has a wall 410' that does not extend laterally side to side as far as the embodiment shown in FIG. 7a. This shortened wall 410', relative to the longer circumferential extension of the proximal and distal flange surfaces 402', 404', allows for lateral spaces 495, 496 flanking the lateral ends of the wall 410'. In some embodiments, these spaces 495, 496 may be used to accommodate syringes having flanges with different shapes, such as the cut flange syringe shown in FIG. 8.

The syringe carrier may have interlocking components in the form of protrusions 425 and indentations 426. The protrusions 425 of the first part of the syringe carrier interlock with the indentations 426 of the second part. These interlocking components may have other snap-fit configurations. Due to the shortened wall 410', the interlocking features are shown defined by the respective flange surfaces 402', 404'. Indeed, the protrusions 425 and indentations 426 are shown defined by the radially inward edges 405', 407' of the corresponding flange surfaces 402' 404'. In one embodiment, the circumferential rounded wall 410' partially surrounds an outer perimeter of the syringe flange 133', and the proximal flange surface 402'of each of the parts together fully overlap a proximal surface 133A' of the syringe flange 133'. As shown in FIG. 8, the distal flange surface 404' of each of the parts together fully overlap the proximal surface 133B' of the syringe flange 133', with the cushion 440 disposed therebetween.

Device 20 may have a delay mechanism that includes a shuttle, generally designated 200, a follower 250 that releasably latches with the shuttle 200, and a dual functioning biasing member 275 acting between the shuttle and the follower. Shuttle 200 may be formed of a proximal shuttle 202 and a distal shuttle 204 further shown in FIG. 10 and FIGS. 11a-11e, respectively, that are fixedly connected during manufacturing assembly. The interaction between the proximal shuttle 202 and the distal shuttle 204, as well as the features of the proximal shuttle 202 are described in greater detail in U.S. Pat. No. 9,872,961.

Distal shuttle 204 includes distal region 270, and the flange 272 that transitions from body 210 to region 270 is designed to engage syringe carrier 185. When the distal shuttle 204 is moved proximally during retraction, the flange 272 abuts against a distal surface of the syringe carrier 185, thus moving the syringe carrier 185 and syringe barrel 132 in the proximal direction with proximal movement of the distal shuttle 204. Groove 280 in distal shuttle body 210 receives a housing key to rotatably fix shuttle 200 with a cavity in sleeve 26. In some embodiments, the device includes a different drive system, where the syringe carrier 185 and syringe barrel may remain stationary (that is, is not proximally moved), and where the syringe carrier still provides a benefit to the syringe flange.

Tabs 282 and 284 radially project from distal region 270 and serve as latching elements or hooks to engage the follower. Notch 286 that leads to pocket 288 within tab 282 receives a proximal projection 289 of the biasing member 275.

An angled, locking latch surface 290 is disposed distally of an opening 292 in line with an axially extending channel 294 formed in the interior surface of distal shuttle body 210. Channel 294 accommodates plunger arm 152 that can project through opening 292 to unlock the locking mechanism described below.

Follower 250 is further shown in FIGS. 12a-12e and includes a proximal portion 298 with ledges 300 and 302 that serve as latching elements that engage shuttle latching tabs 282 and 284. Channel 304 and opening 306 in proximal portion 298 allow axial movement of tabs 282 and 284 therein for manufacturing assembly and for shuttle release relative to the follower during device use. Opening 306 tapers to a slot-shaped portion 310 adapted to closely receive a radial projection 312 of biasing member 275.

A radially projecting flange 316 may snap past snaps in the main body 24 during device assembly. The interior surface of follower portion 298 includes an inwardly projecting ring 318 with a spring centering lip 320. A sleeve shaped distal portion 322 of follower 250 depends from follower portion 298 and has a lesser diameter. Slots 324 in the distal edge of portion 322 define four damping fins 326 of the follower. The slots 324 can be adjusted in size to create to differing delay times. A locking member for follower 250 to limit its rotation relative to the shuttle 200 is formed as a flexure arm 330 with an upwardly extending latch 332 at its end.

Figure 14:
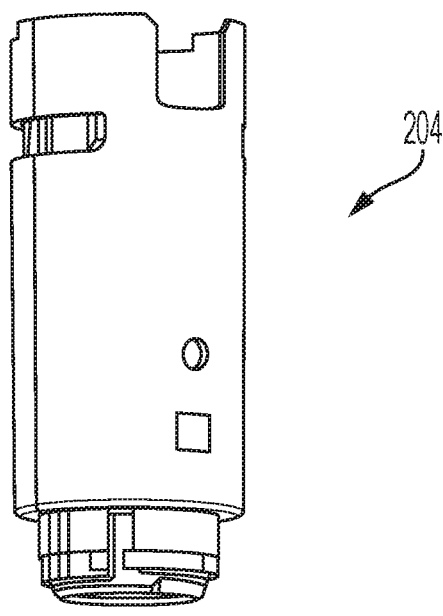
Figure 14:
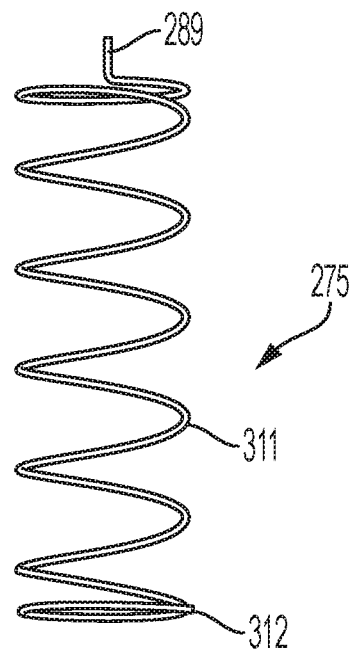
Figure 14:
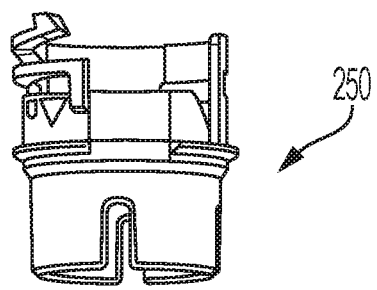

An exploded view of the distal shuttle 204, biasing member 275, and follower 250 is shown in FIG. 14. Biasing member 275 may function as both a torsion spring and a compression spring, with torsional preloading and an axial preloading accomplished during the manufacturing assembly of device 20. Biasing member 275 is shown as a cylindrical spring formed of a helically coiled wire 311, with a shuttle engaging tip in the form of a proximal projection 289, and a follow engaging tip 312.

Figure 13A:
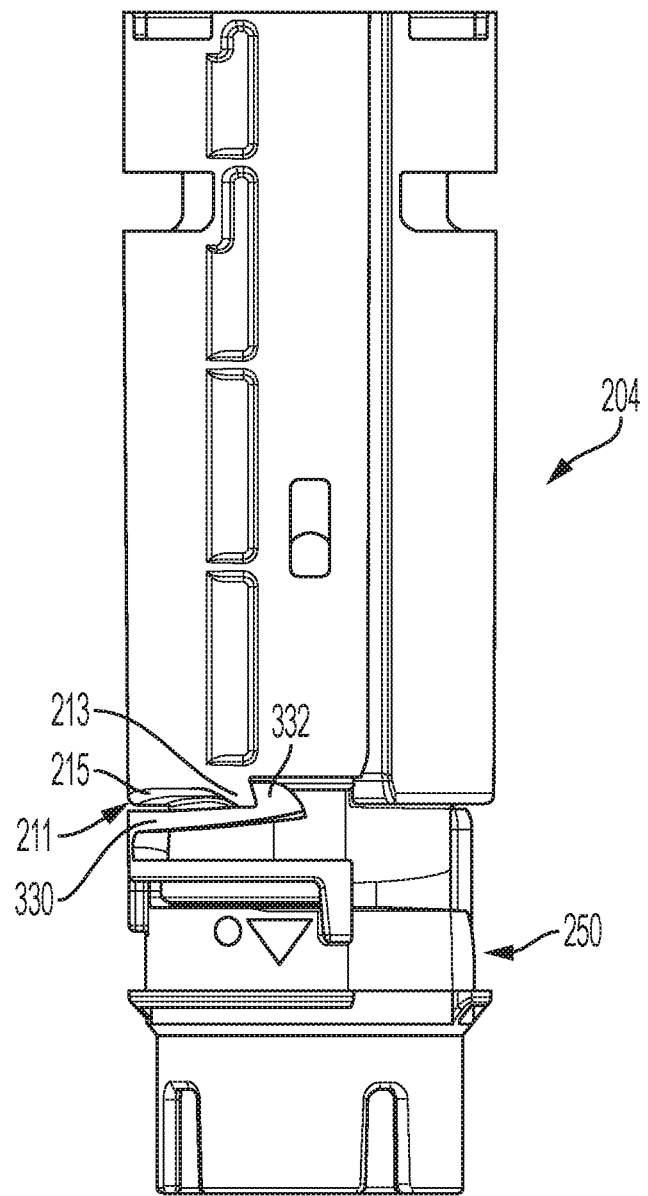
FIG. 13a is an assembly including a distal shuttle and a follower, the follower being shown in the coupled configuration.
Figure 13B:
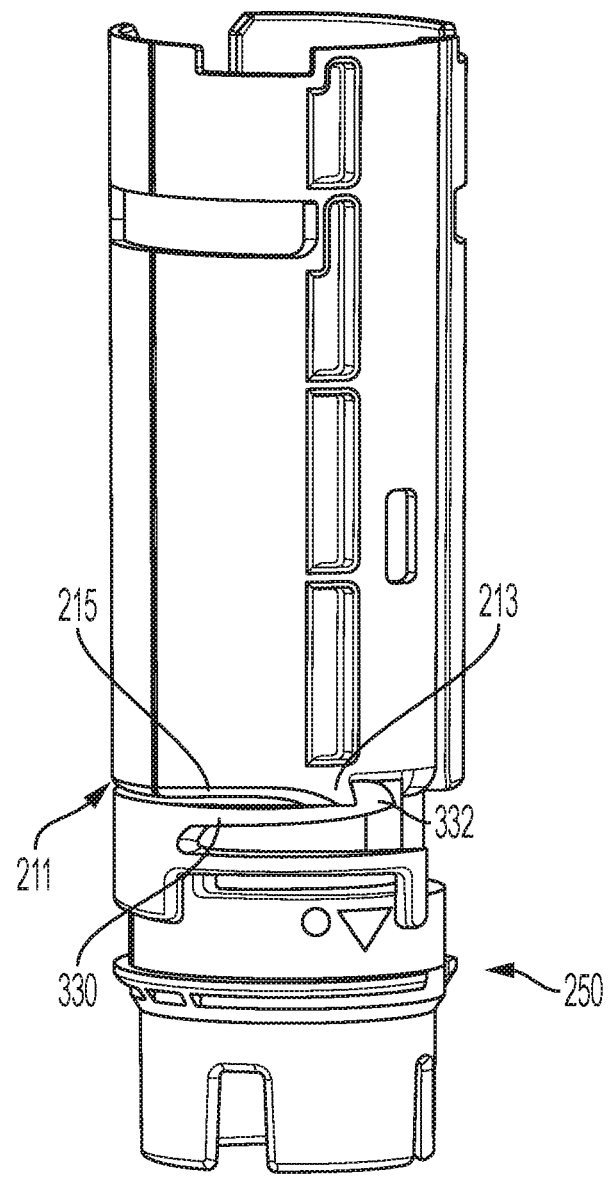
FIG. 13b is a slightly rotated view of the assembly of FIG. 13b to show the interaction between a latch of the follower with a protrusion of the distal shuttle.

An assembly of the distal shuttle 204 and follower 250 shown in a coupled configuration is shown in FIGS. 13a and 13b. In the coupled configuration, the latch 332 of the follower is engaged with a protrusion 213 on a distal surface 211 of the distal shuttle 204.

Figure 15A:
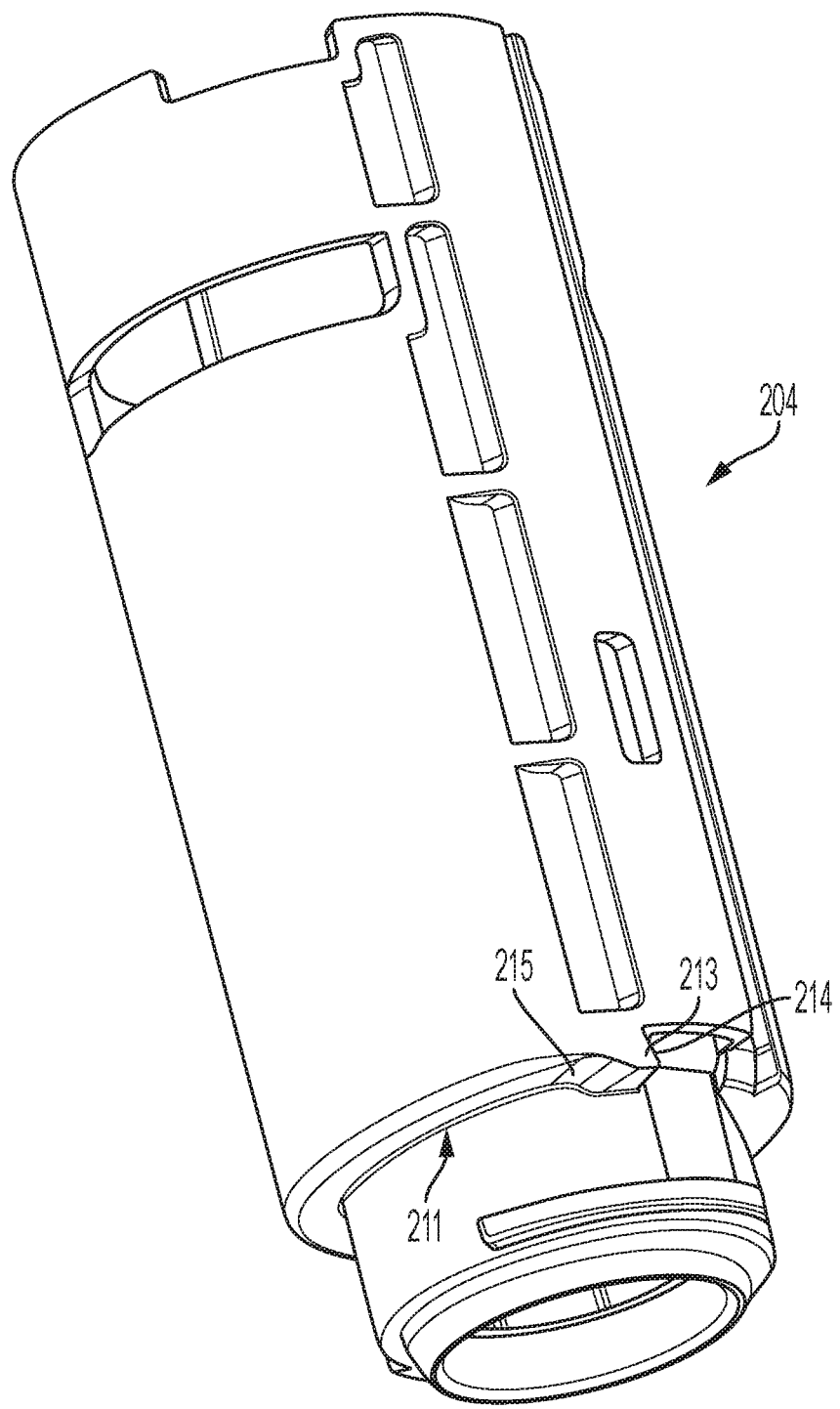
FIG. 15a is a perspective view of a distal shuttle.
Figure 15B:
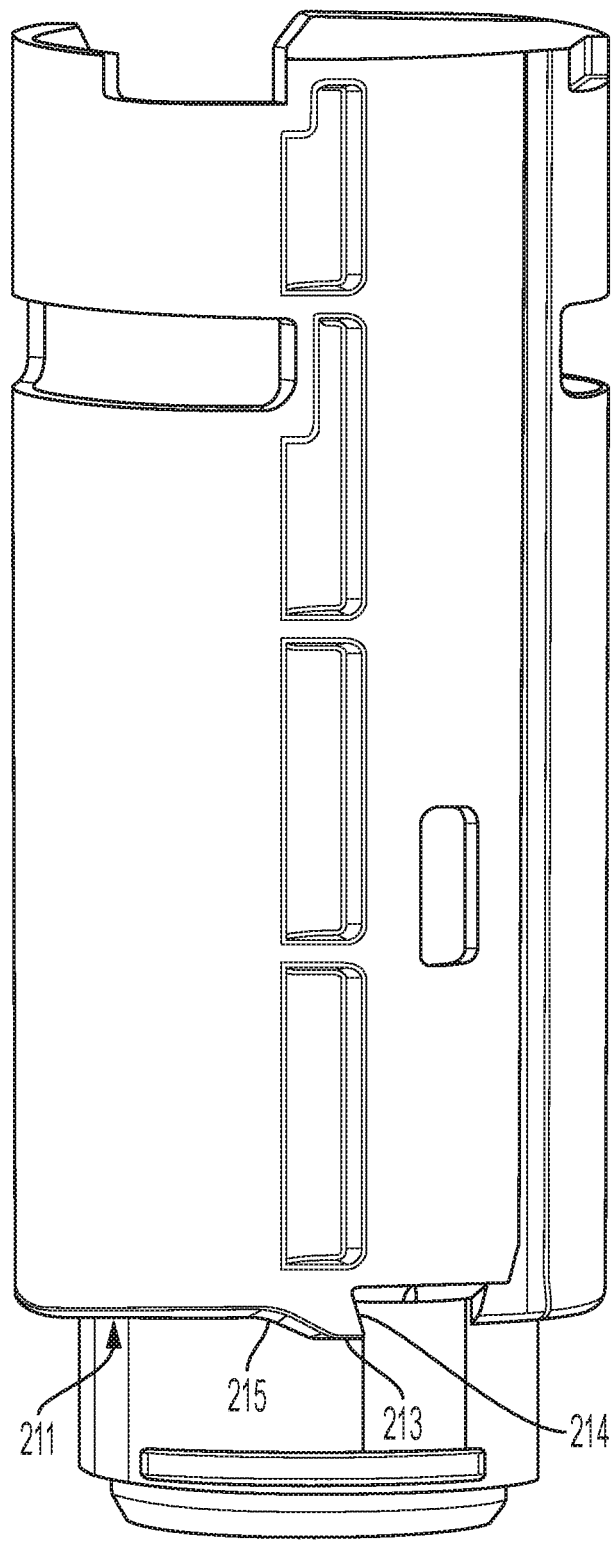

As shown in FIGS. 15a and 15b, the distal surface 211 of the distal shuttle 204 has an undercut region 215 adjacent to the protrusion 213. The undercut region 215 has a curvilinear shape. In some embodiments, the trailing surface 335 may be curved and the undercut region 215 may be curvilinear to facilitate sliding engagement between both.

Figure 12A:
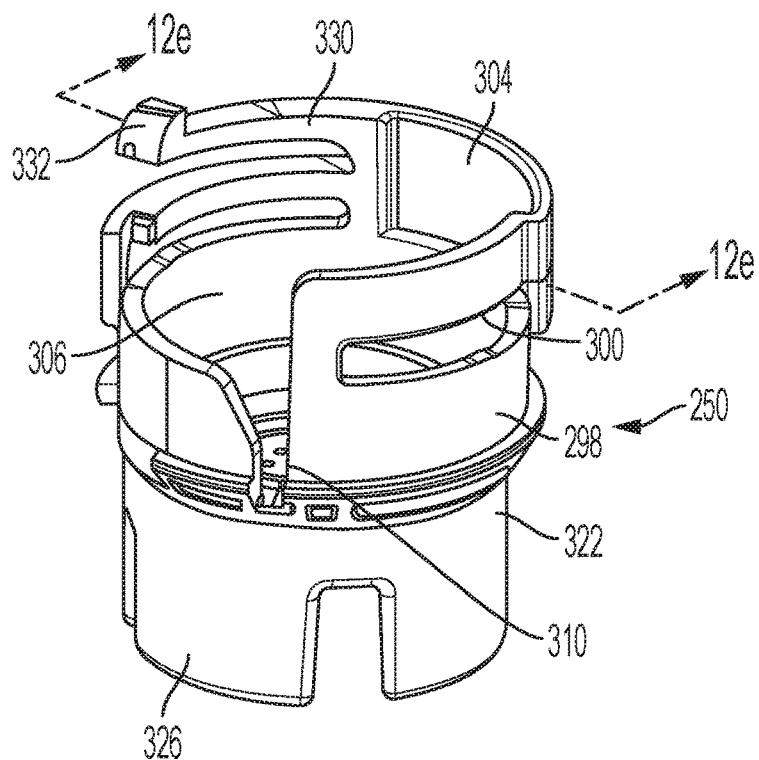
FIGS. 12a, 12b, 12c, 12d and 12e are respectively first perspective, first side, second perspective, second side and longitudinal cross-sectional views of a follower shown separate from the other device components.
Figure 12B:
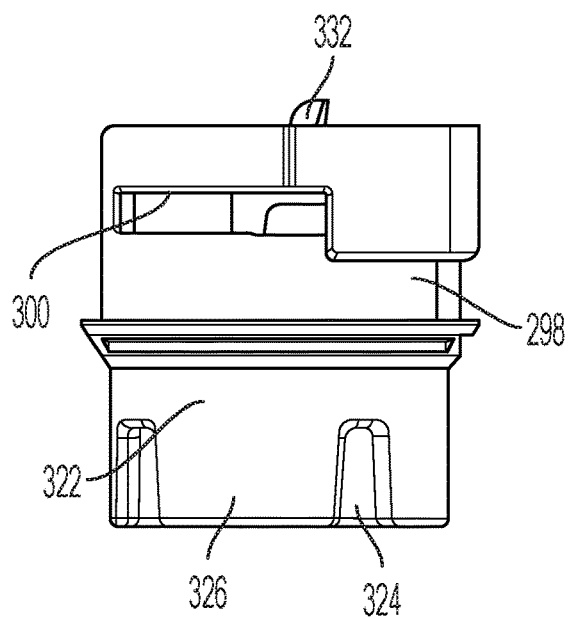
Figure 12C:
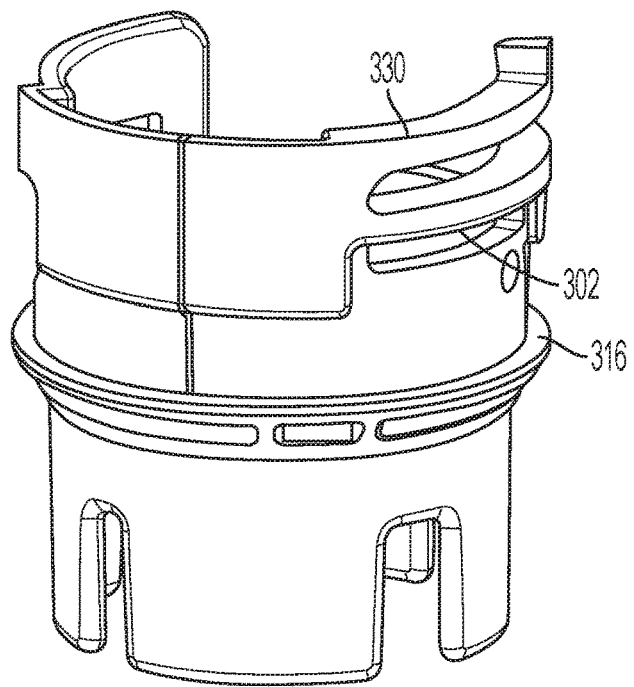
Figure 12D:
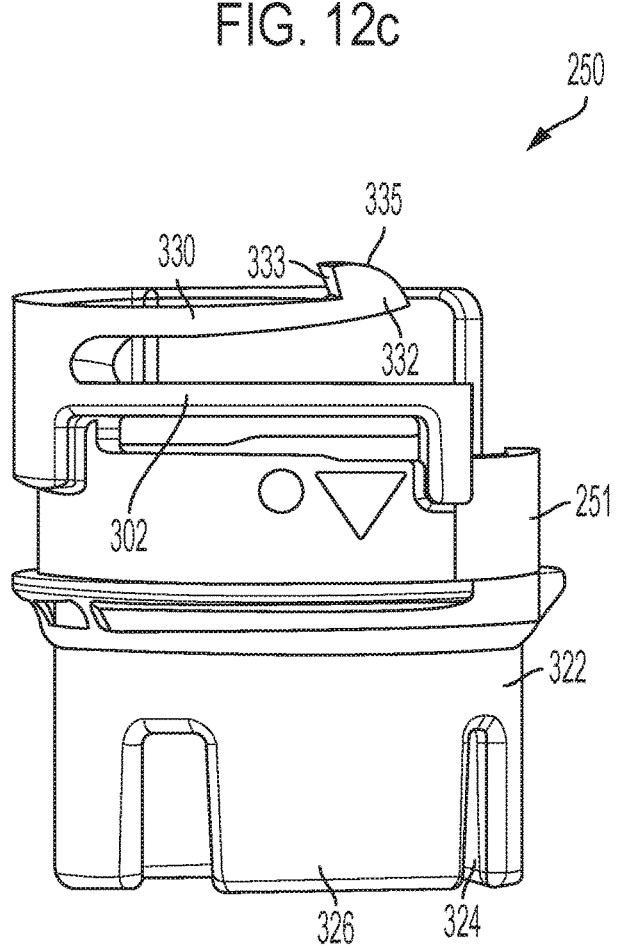
Figure 12E:
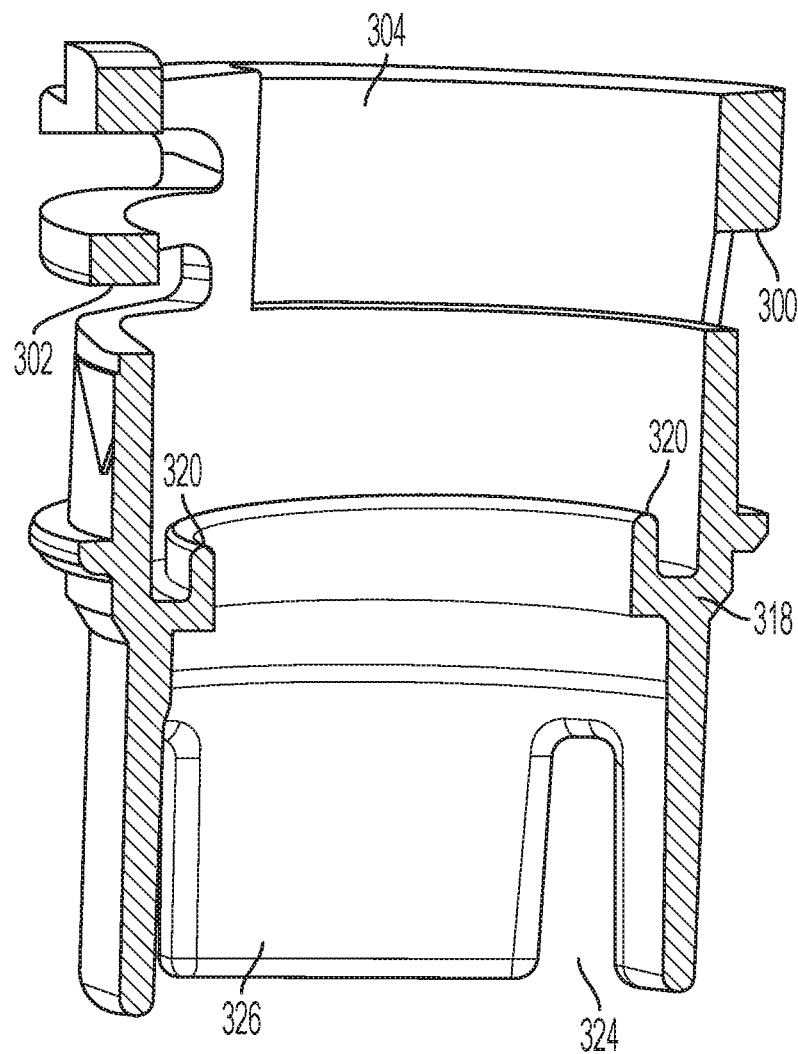

As shown in FIG. 12d, the latch 332 of the follower is axially moveable relative to the follower body 251 due to cantilevered flexure arm 330, which is able to deflect relative to the follower body. The latch 332 may be comprised of a leading surface 333 and a trailing surface 335. The sliding contact between the latch surfaces and the shuttle during rotation of the follower relative to the shuttle can generate friction variability that impede consistent rotation speed of the follower. The leading surface 333 engages with the protrusion 213 when the follower is in the coupled configuration in FIG. 13b. The trailing surface 335 may slidingly engage with the undercut region 215 when the follower is in an uncoupled configuration and is rotating relative to the distal shuttle 204. In the uncoupled configuration, the latch 332 is disengaged with the protrusion 213. In some embodiments, the leading surface 333 may be a flat surface that engages in a confronting relationship a flat surface portion 214 of the protrusion 213. At least one, or both, of the leading surface 333 and flat surface portion 214, may be angled slightly to facilitate latching with and/or uncoupling from the protrusion 213. In some embodiments, the trailing surface 335 may be curved to facilitate uncoupling of the latch from the protrusion, and/or facilitate sliding engagement with the undercut region 215.

Distal shuttle 204 may include a lubricant-infused material to aide in the movement of the distal shuttle 204 within the device housing, particularly during the needle retraction operation. In one example, the entire distal shuttle includes lubricant-infused material. In some embodiments, at least the distal surface 211 of the distal shuttle is made of a lubricant-infused material. Such a material may aid in facilitating uncoupling of the latch 332 from the protrusion 213 and/or facilitating sliding engagement between the latch 332 and the undercut region 215 as the follower 250 rotates relative to the distal shuttle. In some embodiments, the lubricant-infused material may serve to decrease friction and/or friction variability between the distal shuttle and the latch during movement of the follower relative to the distal shuttle. The lubricant-infused material may also serve to lower friction and/or friction variability between the tabs 282, 284 with the ledges 300, 302. In some embodiments, the material may be a silicone-infused material. In some embodiments, the material may be made of polycarbonate with infused silicone of 2%. In some embodiments, all of or at least a portion of the follower 250 may be made of a copolymer to decrease friction and/or friction variability between the distal shuttle and the follower. In some embodiments, at least one of at least the distal surface 211 of the distal shuttle is made of a lubricant-infused material, the trailing surface 335 may be curved, the undercut region 215 may be curvilinear, copolymer follower, or any combination thereof may be employed to provide a retraction assembly for an automatic injection device which can facilitate syringe retraction by decreasing the sliding engagement friction and/or by decreasing friction variation that is generated during retraction. Such embodiments may reduce any frictional delay variability in rotational speed and timing of the follower to a position to allow for shuttle/syringe retraction and/or and more consistent retraction speed and timing at the completion of the delivery cycle, which together may avoid factors contributing to stalled retraction.

Figure 16A:
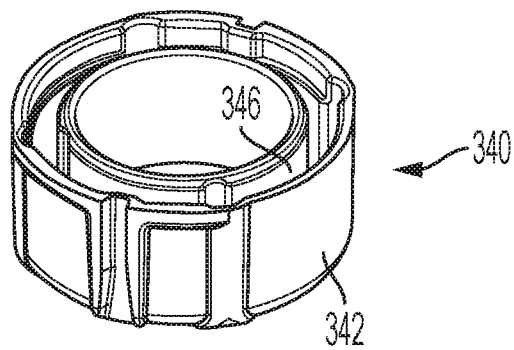
FIGS. 16a and 16b are respectively perspective and side views of a grease collar shown separate from the other device components.
Figure 16B:
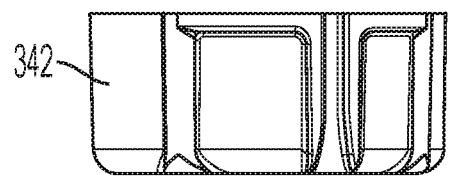

The device may include a grease collar 340, further shown in FIGS. 16a and 16b, that provides a support surface for damping fluid as the follower 250 rotates relative to that support surface. Collar 340 includes an annular body 342 through which fits the syringe barrel. Collar 340 is axially supported within the housing 22. Collar body 342 includes a generally U-shaped wall that defines an annular hollow 346.

A damping compound 350 (shown in FIG. 2), such as a silicone grease thickened with Teflon, may fill annular hollow 346. Follower fins 326 fit within hollow 346 such that compound 350 is disposed both radially inward and outward of such fins 326, as well as between adjacent fins 326 and as a film between the fin undersides and the base of the collar wall, resulting in a damping or delay effect as the follower fins 326 try to rotate relative to the collar.

The construction of device 20 will be further understood in view of a description of one illustrative embodiment of its operation after the end cap is removed in preparation for an injection. To arrange device 20 to inject, sleeve 26, and thereby button 25, is manually rotated by a user to an unlocked state in which the device is ready to inject.

Figure 17:
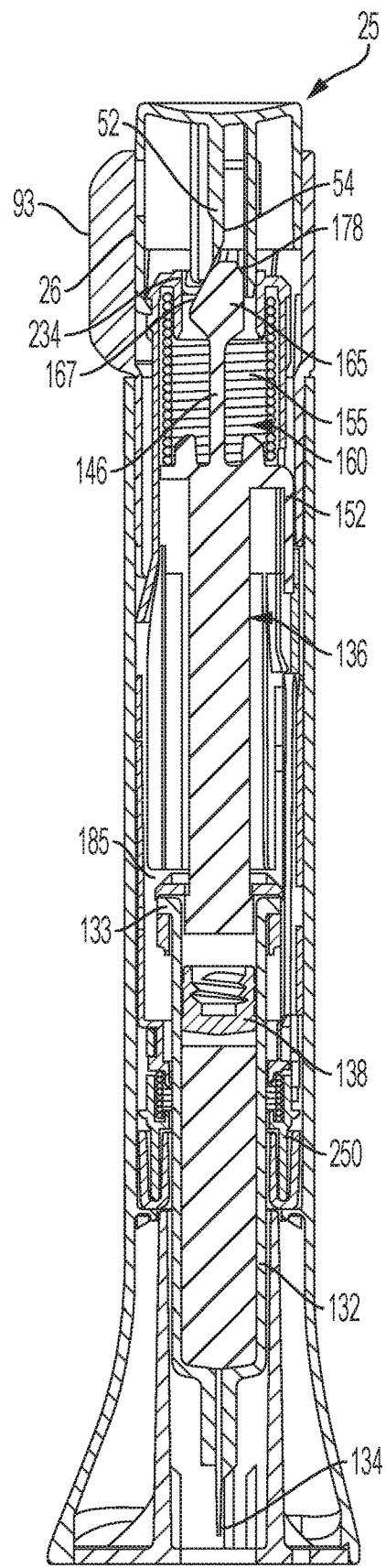
FIG. 17 is a longitudinal cross-sectional view of the automatic injection device in its ready to operate arrangement.

A cross-sectional view of the device in the unlocked state is shown in FIG. 17. When a user subsequently applies a distal force on button 25, button 25 starts to move downward into sleeve 26, thereby driving flange surface 54 against ramp surface 167. As button 25 continues to move further distally, with flange portion 52 inserting further into the shuttle opening, flange surface 54 slides along ramp surface 167. During this sliding, flange portion 52 cams prong 160 radially outward because flange portion 52 is prevented from bending in the opposite radially outward direction due to the contact with the supportive collar surface 234. Flange portion 52 is prevented from twisting due to contact with supportive surfaces on the proximal shuttle 202. Prong 160 can be cammed outward as finger 162 bends until latching surfaces 172 disengage from latch surfaces on the proximal shuttle, at which point the proximal-most portion of plunger prong 160 passes downward through the shuttle due to spring 155 directly biasing the plunger element 136 downward to drive the plunger element and thereby the piston 138 distally, which driven motion shifts syringe barrel 132 and syringe carrier 185 distally relative to the shuttle and the housing to cause the tip of needle 134 to project beyond the housing distal end for penetrating a user's skin, and then forces the medication contents of the syringe through that needle for an injection.

Figure 18:
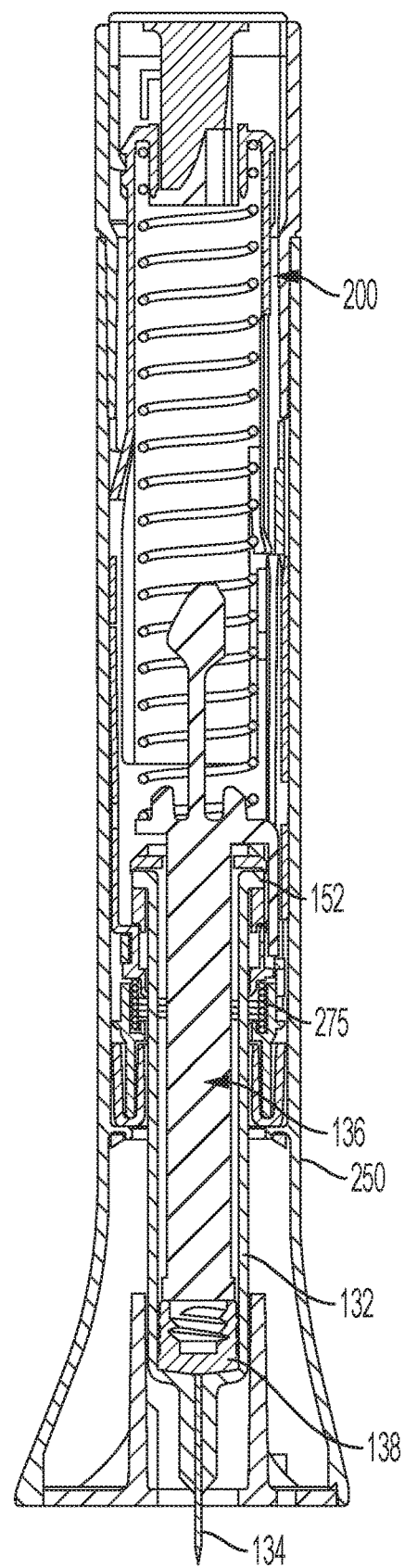
FIG. 18 is a longitudinal cross-sectional view of the automatic injection device after the automatic injection device has been triggered for injection.

As plunger element 136 moves distally during medication injection, the arm 152 abuts against the latch 332 of the follower 250, causing flexure arm 330 to deflect distally, causing the leading surface 333 of the latch to slide distally past the protrusion 213 of the distal shuttle 204, thus causing the latch 332 to clear the protrusion 213. With the latch 332 disengaged from the protrusion 213 of the distal shuttle 204, the follower 250 is in the uncoupled configuration, and the follower 250 is thus unlocked for rotation relative to the distal shuttle 204. FIG. 18 shows the arrangement of device 20 at this point of the use process.

Follower 250, as urged by the torsional preloading of biasing member 275, rotates against the damping effect of damping compound 350, during which rotation remaining medication can be properly expelled from the syringe through the needle. When follower 250 has rotated such that shuttle tabs 282 and 284 are clear of ledges 300 and 302, shuttle 200 and follower 250 are thereby unlatched so as to allow the compressively preloaded biasing member 275 to decompress, forcing shuttle 200 proximally to retract the syringe carrier 185 and the syringe barrel 132 along with the syringe carrier, thereby retracting the distal tip of the injection needle 134 to a protected, retracted position within the housing 22.

While the automatic injection device described herein has been shown and described as having preferred designs, the present device may be modified within the spirit and scope of this disclosure. For example, while the biased element that the trigger assembly releases in the shown embodiment is the plunger that itself contacts the syringe piston, the trigger assembly could be used to release different biased elements in alternate embodiments, or elements that are biased with parts different than coiled springs. This application is therefore intended to cover any variations, uses or adaptations of the device using its general principles. Further, this application is intended to cover such departures from the present disclosure as come within known or customary practice in the art to which this automatic injection device pertains.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

Various aspects are described in this disclosure, which include, but are not limited to, the following aspects:

1. An automatic injection device, including: a housing including a proximal end and a distal end; a syringe including a needle, a syringe body and a plunger, the syringe being moveable within the housing from a first position to a second position that is distal to the first position to move the needle toward the distal end of the housing, and the plunger being moveable relative to the syringe body to expel medication from the syringe body through the needle; a syringe carrier including a first part and a second part that are identical to one another, are discrete from one another, and are interlocked together, each of the first and second parts including: a proximal flange surface; a distal flange surface; a circumferential rounded wall between the proximal flange surface and the distal flange surface; and a gap located between the proximal flange surface, the distal flange surface and the circumferential rounded wall, wherein a portion of the syringe body is received within the gap.

2. The automatic injection device of aspect 1, wherein each of the first and second parts of the syringe carrier includes a protruding prong that interlocks with the other of the first and second parts.

3. The automatic injection device of any one of aspects 1-2, wherein the syringe carrier includes a cushion, the proximal flange surface and the distal flange surface having a greater material hardness than the cushion.

4. The automatic injection device of aspect 3, wherein the syringe body includes a syringe body flange, and the cushion is in contact with the syringe body flange.

5. The automatic injection device of aspect 3, wherein the cushion includes at least one radial protrusion extending from an inner radial surface of the cushion.

6. The automatic injection device of any one of aspects 1-5, wherein the syringe body includes a syringe body flange, wherein the circumferential rounded wall of the syringe carrier partially surrounds an outer perimeter of the syringe flange, and the proximal flange surface of each of the parts together fully overlap a proximal surface of the syringe flange.

7. The automatic injection device of any one of aspects 1-6, wherein the syringe body includes a syringe body flange, wherein the proximal flange surface of each of the parts together fully overlap a proximal surface of the syringe flange.

8. The automatic injection device of any one of aspects 1-7, wherein the syringe carrier fully surrounds an outer perimeter of the syringe body.

9. The automatic injection device of any one of aspects 1-8, wherein each of the first and second parts of the syringe carrier includes a first lateral wall end and a second lateral wall end, the circumferential rounded wall extending from the first lateral wall end to the second lateral wall end, the first lateral wall end having a prong, and the second lateral wall end having a latch protrusion, wherein the prong of the first part of the syringe carrier interlocks with the latch protrusion of the second part of the syringe carrier.

10. An automatic injection device, including: a housing including a proximal end and a distal end; a syringe including a needle, a syringe body and a plunger, the syringe body including a syringe flange extending radially from the syringe body, and the plunger being moveable relative to the syringe body to expel medication from the syringe body through the needle; a syringe carrier including a first part and a second part that are discrete from one another, and are interlocked together, each of the first and second parts including: a proximal flange surface; a distal flange surface; a circumferential rounded wall extending between the proximal flange surface and the distal flange surface; a cushion disposed along a distal flange surface, the proximal flange surface and the distal flange surface having a greater material hardness than the cushion; and a gap defined by the proximal flange surface, the cushion, and the circumferential rounded wall, receiving a portion of the syringe flange, wherein the cushions of each of the first and second parts together defining a ring shape to provide full circumferential support along the syringe flange.

11. The automatic injection device of aspect 10, wherein the cushion includes at least one protrusion contacting the syringe body underneath the syringe flange, flange, wherein the at least one protrusion is disposed adjacent to an end of an inner radial surface of the cushion of each of the first and second parts.

12. The automatic injection device of any one of aspects 10-11, wherein the first part and the second part are identical to one another, each of the first and second parts having interlocking elements configured to couple to one another, and walls defining together an opening surrounding the moveable plunger.

13. An automatic injection device, including: a housing including a proximal end and a distal end; a syringe including a needle, a syringe body and a plunger, the syringe being moveable within the housing from a first position to a second position that is distal to the first position to move the needle toward the distal end of the housing, and the plunger being moveable relative to the syringe body to expel medication from the syringe body through the needle; a shuttle having a distal surface including a protrusion and a curvilinear surface, the curvilinear surface extending from the protrusion to define an undercut region, at least a portion of the distal surface being made of a lubricant-infused material; and a follower having a follower body and a latch, the latch being moveable relative to the follower body and relative to the protrusion of the shuttle; wherein: the follower has a coupled configuration in which the latch is biasedly coupled over the protrusion, and the follower has a decoupled configuration in which the latch has cleared the protrusion and is in sliding engagement with the curvilinear surface, the follower is rotatable relative to the shuttle, and the shuttle is moveable toward the proximal end of the housing to retract the syringe.

14. The automatic injection device of aspect 13, wherein the latch includes a cantilevered arm with an end having a protrusion.

15. The automatic injection device of aspect 14, wherein the protrusion has a straight leading surface and a curved trailing surface, wherein the straight leading surface is in contact with the protrusion when the follower is in the coupled configuration, and the curved trailing surface is in contact with the curvilinear surface when the follower is in the decoupled configuration.

16. The automatic injection device of any one of aspects 13-15, wherein the lubricant-infused material includes silicone.

17. The automatic injection device of any one of aspects 13-16, wherein the entire shuttle is made of the lubricant-infused material.

18. The automatic injection device of any one of aspects 13-17, further including a spring that is compressed between the shuttle and the follower when the follower is in the coupled configuration.

19. The automatic injection device of aspect 18, wherein the spring is torsionally pre-loaded when the follower is in the coupled configuration.

20. The automatic injection device of any one of aspects 13-19, wherein the shuttle is moveable toward the proximal end of the housing after the follower has rotated through a predetermined angle of rotation.

21. The automatic injection device of aspects 1, 11 or 13, wherein the syringe body contains a medication.

22. The automatic injection device of aspects 1 and 11 may be combined together alone, or along with any other aspects described herein.

What is claimed is:
1. An automatic injection device, comprising:
a housing comprising a proximal end and a distal end;

a syringe including a needle, a syringe body and a plunger, the syringe being moveable within the housing from a first position to a second position that is distal to the first position to move the needle toward the distal end of the housing, and the plunger being moveable relative to the syringe body to expel medication from the syringe body through the needle;

a shuttle having a distal surface comprising a shuttle protrusion and a curvilinear surface, the curvilinear surface extending from the shuttle protrusion to define an undercut region, at least a portion of the distal surface being made of a lubricant-infused material; and a follower having a follower body and a latch, the latch having a cantilevered arm being moveable relative to the follower body and relative to the shuttle protrusion, the cantilevered arm with an end having a latch protrusion, wherein the latch protrusion has a straight leading surface and a curved trailing surface;

wherein:

the follower has a coupled configuration in which the latch is biasedly coupled over the shuttle protrusion and the straight leading surface of the latch protrusion is in contact with the shuttle protrusion, and the follower has a decoupled configuration in which the latch has cleared the shuttle protrusion and the curved trailing surface of the latch protrusion is in sliding engagement with the curvilinear surface, the follower is rotatable relative to the shuttle, and the shuttle is moveable toward the proximal end of the housing to retract the syringe.

2. The automatic injection device of claim 1, wherein the lubricant-infused material comprises silicone.

3. The automatic injection device of claim 1, wherein the entire shuttle is made of the lubricant-infused material.

4. The automatic injection device of claim 1, further comprising a spring that is compressed between the shuttle and the follower when the follower is in the coupled configuration.

5. The automatic injection device of claim 4, wherein the spring is torsionally pre-loaded when the follower is in the coupled configuration.

6. The automatic injection device of claim 1, wherein the shuttle is moveable toward the proximal end of the housing after the follower has rotated through a predetermined angle of rotation.

7. The automatic injection device of claim 1, wherein the syringe body contains a medication.

8. The automatic injection device of claim 1, further comprising a syringe carrier including a first part and a second part that are discrete from one another and interlocked together, each of the first and second parts comprising a proximal flange surface, a distal flange surface, a circumferential rounded wall between the proximal flange surface and the distal flange surface, and a gap located between the proximal flange surface, the distal flange surface and the circumferential rounded wall, wherein a portion of the syringe body is received within the gap, wherein the shuttle is engageable with the syringe carrier during proximal movement.

9. The automatic injection device of claim 8, wherein the syringe carrier includes a cushion, the proximal flange surface and the distal flange surface having a greater material hardness than the cushion.

10. The automatic injection device of claim 9, wherein the syringe body includes a syringe body flange, and the cushion is in contact with the syringe body flange.

11. The automatic injection device of claim 10, wherein the cushion includes at least one cushion protrusion contacting the syringe body underneath the syringe body flange, wherein the at least one cushion protrusion is disposed adjacent to an end of an inner radial surface of the cushion of each of the first and second parts.

12. The automatic injection device of claim 8, wherein the syringe body includes a syringe body flange, wherein the circumferential rounded wall of the syringe carrier partially surrounds an outer perimeter of the syringe body flange, and said proximal flange surface of each of the parts together fully overlap a proximal surface of the syringe body flange.

13. An automatic injection device, comprising:

a housing comprising a proximal end and a distal end;

a syringe including a needle, a syringe body and a plunger, the syringe being axially moveable within the housing from a first position to a second position that is distal to the first position to move the needle toward the distal end of the housing, and the plunger being axially moveable relative to the syringe body to expel medication from the syringe body through the needle;

a shuttle coupled to the syringe, the shuttle having a distal surface comprising a shuttle protrusion and a curvilinear surface, the curvilinear surface extending from the shuttle protrusion to define an undercut region; and a follower having a follower body and a latch, the latch being moveable relative to the follower body and relative to the shuttle protrusion, the latch comprising a latch protrusion, the latch protrusion having a straight leading surface and a curved trailing surface;

wherein:

the follower has a coupled configuration in which the latch of the follower is biasedly coupled with the shuttle protrusion to inhibit rotation of the follower, the straight leading surface of the latch protrusion is in contact with the shuttle protrusion, and the follower has a decoupled configuration in which the latch protrusion has cleared the shuttle protrusion and the curved trailing surface of the latch protrusion is in sliding engagement with the curvilinear surface of the shuttle as the follower is rotated relative to the shuttle, the shuttle axially moveable toward the proximal end of the housing to retract the syringe after the follower has rotated through a predetermined angle of rotation.

14. The automatic injection device of claim 13, wherein the distal surface of the shuttle is made of a lubricant-infused material.

15. The automatic injection device of claim 13, further comprising a syringe carrier including a first part and a second part that are discrete from one another and interlocked together, each of the first and second parts comprising a proximal flange surface, a distal flange surface, a circumferential rounded wall between the proximal flange surface and the distal flange surface, and a gap located between the proximal flange surface, the distal flange surface and the circumferential rounded wall, wherein the syringe body comprises a syringe flange that is received within the gap, wherein the shuttle is engaged with the syringe carrier during proximal movement when the syringe being retracted.

16. The automatic injection device of claim 15, wherein the syringe carrier includes a cushion, the proximal flange surface and the distal flange surface having a greater material hardness than the cushion, wherein the cushion is in contact with the syringe flange.

17. The automatic injection device of claim 13, further comprising a spring that is compressed between the shuttle and the follower when the follower is in the coupled configuration.

18. The automatic injection device of claim 17, wherein the spring is torsionally pre-loaded when the follower is in the coupled configuration, and the spring urges rotation of the follower relative to the shuttle when the follower is in the decoupled configuration.

19. The automatic injection device of claim 13, wherein the syringe body contains a medication.

* * * * *